(12) United States Patent
Banerjee et al.

(10) Patent No.: US 12,194,294 B2
(45) Date of Patent: Jan. 14, 2025

(54) ORAL DRUG DELIVERY DEVICES AND METHODS USING IONTOPHORESIS

(71) Applicants: The Regents of the University of California, Oakland, CA (US); President and Fellows of Harvard College, Cambridge, MA (US)

(72) Inventors: Amrita Banerjee, Fargo, ND (US); Renwei Chen, Santa Barbara, CA (US); Shamsul Arafin, Goleta, CA (US); Samir Mitragotri, Lexington, MA (US)

(73) Assignees: The Regents of the University of California, Oakland, CA (US); President and Fellows of Harvard College, Cambridge, MA (US)

( * ) Notice: Subject to any disclaimer, the term of this patent is extended or adjusted under 35 U.S.C. 154(b) by 570 days.

(21) Appl. No.: 16/775,515

(22) Filed: Jan. 29, 2020

(65) Prior Publication Data

US 2020/0238081 A1 Jul. 30, 2020

Related U.S. Application Data

(60) Provisional application No. 62/798,373, filed on Jan. 29, 2019.

(51) Int. Cl.
*A61N 1/32* (2006.01)
*A61N 1/05* (2006.01)

(52) U.S. Cl.
CPC ........... *A61N 1/325* (2013.01); *A61N 1/0509* (2013.01); *A61N 1/0548* (2013.01)

(58) Field of Classification Search
CPC ..... A61N 1/325; A61N 1/0509; A61N 1/0548
See application file for complete search history.

(56) References Cited

U.S. PATENT DOCUMENTS

2002/0183686 A1* 12/2002 Darvish ................. A61N 1/327
604/95.05
2005/0058701 A1* 3/2005 Gross .................... A61K 9/0097
374/E13.002

(Continued)

FOREIGN PATENT DOCUMENTS

WO WO-2018213600 A1 * 11/2018 ............. A61B 10/02

OTHER PUBLICATIONS

Alkilani et al. "Transdermal drug delivery: innovative pharmaceutical developments based on disruption of the barrier properties of the stratum corneum." Pharmaceutics 7(4): 438-470 (2015).

(Continued)

*Primary Examiner* — Mallika D Fairchild
(74) *Attorney, Agent, or Firm* — Nixon Peabody LLP; David S. Resnick; Nicole D. Kling

(57) ABSTRACT

Disclosed herein are methods, systems, and devices for oral drug delivery. The method generally involves orally administering a drug delivery device to the subject in need of treatment and triggering iontophoresis. The drug delivery device includes one or more active agents for delivery to the subject. The method can include the step of delivering the active agent to the intestinal mucosa after iontophoresis is triggered at the site, or simultaneously as iontophoresis is applied at the site. After the active agent(s) are delivered, the drug delivery device can be released from the intestinal mucosa. The iontophoresis can be performed for a period of time and at an electrical current that is effective to improve permeability of the one or more active agents across the intestine compared to orally administering the same drug delivery device in the absence of iontophoresis.

17 Claims, 8 Drawing Sheets

Specification includes a Sequence Listing.

(56) References Cited

U.S. PATENT DOCUMENTS

2008/0188837 A1* 8/2008 Belsky ............... A61K 9/0097
604/890.1
2013/0337022 A1* 12/2013 Pillay ..................... A61K 9/00
514/423

OTHER PUBLICATIONS

Brown et al. "Dermal and transdermal drug delivery systems: current and future prospects." Drug Delivery 13(3): 175-187 (2006).
Chaturvedula et al. "In vivo iontophoretic delivery and pharmacokinetics of salmon calcitonin." International Journal of Pharmaceutics 297(1-2): 190-196 (2005).
Chen et al. "Iontophoresis-driven penetration of nanovesicles through microneedle-induced skin microchannels for enhancing transdermal delivery of insulin." Journal of Controlled Release 139(1): 63-72 (2009).
Chen et al. "Short-duration ocular iontophoresis of ionizable aciclovir prodrugs: A new approach to treat herpes simplex infections in the anterior and posterior segments of the eye." International Journal of Pharmaceutics 536(1): 292-300 (2018).
Dixit et al. "Iontophoresis—an approach for controlled drug delivery: a review." Current Drug Delivery 4(1): 1-10 (2007).
Dubey et al. "Electrically-assisted delivery of an anionic protein across intact skin: cathodal iontophoresis of biologically active ribonuclease T1." Journal of Controlled Release 152(3): 356-362 (2011).
Gaillard-Bigot et al. "Vascular effects of treprostinil cutaneous iontophoresis on the leg, finger, and foot." The Journal of Clinical Pharmacology 57(9): 1215-1220 (2017).
Green. "Iontophoretic delivery of peptide drugs." Journal of Controlled Release 41(1-2): 33-48 (1996).
Huang et al. "Transdermal iontophoretic delivery of thyrotropin-releasing hormone across excised rabbit pinna skin." Drug Development and Industrial Pharmacy 22(11): 1075-1081 (1996).
Jacoby et al. "Vaginal iontophoresis of a choline compound." American Journal of Obstetrics and Gynecology 44(2): 250-258 (1942).
Kalia et al. "Iontophoretic drug delivery." Advanced Drug Delivery Reviews 56(5): 619-658 (2004).
Kalluri et al. "Transdermal delivery of proteins." Aaps Pharmscitech 12(1): 431-441 (2011).
Korsten et al. "Delivery of neostigmine and glycopyrrolate by iontophoresis: a nonrandomized study in individuals with spinal cord injury." Spinal Cord 56(3): 212-217 (2018).
Lee et al. "MEMS devices for drug delivery." Advanced Drug Delivery Reviews 128: 132-147 (2018).
Leonard et al. "Evaluation of the Caco-2 monolayer as a model epithelium for iontophoretic transport." Pharmaceutical Research 17(10): 1181-1188 (2000).
Leonard et al. "Iontophoresis-enhanced absorptive flux of polar molecules across intestinal tissue in vitro." Pharmaceutical Research 17(4): 476-478 (2000).
Martanto et al. "Transdermal delivery of insulin using microneedles in vivo." Pharmaceutical Research 21(6): 947-952 (2004).
Mitragotri. "Current status and future prospects of needle-free liquid jet injectors." Nature Reviews Drug Discovery 5(7): 543-548 (2006).
Myles et al. "Recent progress in ocular drug delivery for posterior segment disease: emphasis on transscleral ontophoresis." Advanced Drug Delivery Reviews 57(14): 2063-2079 (2005).
Pan et al. "The enhancing effect of electroporation and iontophoresis on the permeation of insulin through human skin." Yao Xue Xue Bao= Acta Pharmaceutica Sinica 37(8): 649-652 (2002) [English Abstract].
Pillai et al. "Transdermal iontophoresis of insulin: IV. Influence of chemical enhancers." International Journal of Pharmaceutics 269(1): 109-120 (2004).
Ren et al. "Characterization of cornified oral mucosa for iontophoretically enhanced delivery of chlorhexidine." European Journal of Pharmaceutics and Biopharmaceutics 99: 35-44 (2016).
Shoeibi et al. "Iontophoresis in ophthalmology: A review of the literature." Reviews in Clinical Medicine 1(4): 183-188 (2014).
Tokumoto et al. "Effect of electroporation and pH on the iontophoretic transdermal delivery of human insulin." International Journal of Pharmaceutics 326(1-2): 13-19 (2006).
Traverso et al. "Microneedles for drug delivery via the gastrointestinal tract." Journal of Pharmaceutical Sciences 104(2): 362-367 (2015).
Kitian et al. "A novel remote controlled capsule for site-specific drug delivery in human GI tract." International Journal of Pharmaceutics 382(1-2): 160-164 (2009).
Zhang et al. "Oral mucosal drug delivery: clinical pharmacokinetics and therapeutic applicaitons." Clinical Pharmacokinetics 41(9): 661-680 (2002).
Zhang, et al. "A flexible device for ocular iontophoretic drug delivery." Biomicrofluidics 10(1): 011911 (2016).
Zhuang et al. "A MEMS-based electronic capsule for time controlled drug delivery in the alimentary canal." Sensors and Actuators A: Physical 169(1): 211-216 (2011).

* cited by examiner

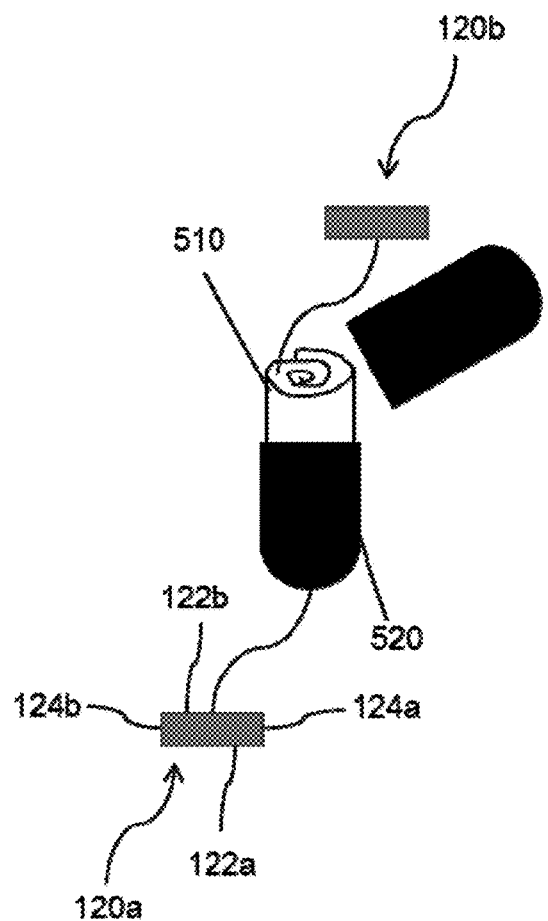
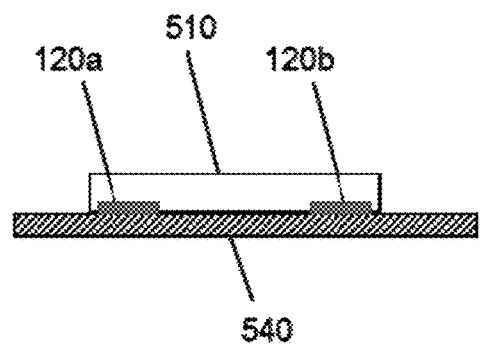
FIG. 13A  FIG. 13B
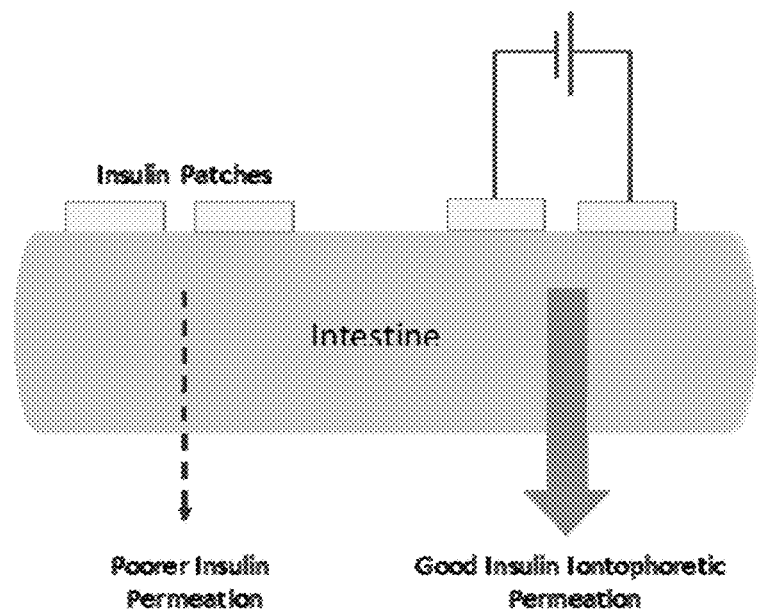
FIG. 14A

ORAL DRUG DELIVERY DEVICES AND METHODS USING IONTOPHORESIS

CROSS-REFERENCE TO RELATED APPLICATIONS

This application claims benefit under 35 U.S.C. § 119(e) of U.S. Provisional Application No. 62/798,373 filed Jan. 29, 2019, the contents of which are incorporated herein by reference in their entirety.

STATEMENT REGARDING FEDERALLY SPONSORED RESEARCH

This invention was made with Government support under Grant No. 1R01DK097379-01A1 awarded by National Institutes of Health. The Government has certain rights in the invention.

SEQUENCE LISTING

The instant application contains a Sequence Listing which has been filed electronically in ASCII format and is hereby incorporated by reference in its entirety. Said ASCII copy, created on Jan. 31, 2020, is named 002806-096890USPT_SL.txt and is 2,991 bytes in size.

FIELD OF THE INVENTION

The field of the invention is generally methods and devices for oral drug delivery.

BACKGROUND OF THE INVENTION

Oral delivery is a favored route for drug administration by both patients and physicians due to its ease of administration. However, its use for biologics is limited because they are susceptible to gastrointestinal degradation, undergo proteolytic cleavage by intestinal enzymes and have low permeability across the intestinal wall. This results in almost negligible oral bioavailability of such drugs (Goldberg, et al., "Challenges for the oral delivery of macromolecules", *Nat Rev Drug Discov.,* 2(4):289-95 (2003)). This necessitates parenteral delivery of these therapeutic macromolecules, which lacks patient compliance and often results in non-adherence to dosing regimen, especially in the long-term.

Although effective to various extents, there is still an unmet medical need for developing technologies that improve oral delivery of biologics.

Different approaches for improving the oral delivery of biologics have been investigated, including modification of protein/peptide structure to impart resistance to degradation by gastrointestinal acids and enzymes and/or improve permeability across intestinal wall, encapsulating them in enterically coated carriers or other formulations, using permeation enhancers and proteolytic inhibitors (Shaji, et al., "Protein and Peptide drug delivery: oral approaches" *Indian J Pharm Sci.,* 70(3):269-77 (2008); Fonte, et al., "Oral insulin delivery: how far are we?" *J Diabetes Sci. Technol.,* 7(2):520-31 (2013)). Nevertheless, there is still an unmet medical need to improve oral delivery of biologics and other active agents.

Therefore, it is an object of the present invention to provide methods for improving oral delivery of therapeutics and biologics. It is a further object of the present invention to provide systems and/or devices for improving oral delivery of therapeutics and biologics.

SUMMARY OF THE INVENTION

Methods, systems, and devices for oral drug delivery to a subject in need thereof are disclosed herein. Optionally, the subject in need of treatment has type 1 or type 2 diabetes.

The method generally involves orally administering a drug delivery device to the subject in need of treatment and triggering iontophoresis. The drug delivery device includes one or more active agents for delivery to the subject. Iontophoresis can be triggered in a variety of manners, such as via an environmental stimulus, such as change in pH or temperature, a timer, or a remote control. Optionally, the drug delivery device adheres to the intestinal mucosa.

The method can include the step of delivering the active agent to the intestinal mucosa after iontophoresis is triggered at the site. Optionally, the active agent is delivered simultaneously as iontophoresis is applied at the site.

After the active agent(s) are delivered, the drug delivery device can be released from the intestinal mucosa. The drug delivery device can be released by any suitable process, such as disintegration, loss of adhesion to the intestinal mucosa, or a combination thereof.

The iontophoresis can be performed for a period of time and at an electrical current that is effective to improve permeability of the one or more active agents across the intestine compared to orally administering the same drug delivery device in the absence of iontophersis.

The oral drug delivery device can be administered to improve transport and bioavailability of one or more active agents compared to the same formulation administered in the absence of iontophoresis. The oral drug delivery device can be a micro-electro-mechanical system (MEMS) based device. Exemplary oral drug delivery devices contain a mucoadhesive patch and two or more electrodes. Generally, the mucoadhesive patch comprises the active agent(s) to be delivered. The active agent can be a small molecule or a macromolecule, such as a protein or a peptide, preferably insulin or an analog thereof. The active agent(s) can be present in an effective amount to reduce blood glucose levels.

In one aspect of any of the embodiments, described herein is a method for oral drug delivery of an active agent to a subject in need thereof comprising: a) orally administering an iontophoretic drug delivery device to the subject, wherein the iontophoretic drug delivery device comprises the active agent. In one aspect of any of the embodiments, described herein is a method for oral drug delivery of an active agent to a subject in need thereof comprising: a) orally administering a drug delivery device to the subject, wherein the drug delivery device comprises the active agent; and b) triggering iontophoresis.

In some embodiments of any of the aspects, the iontophoresis is triggered by an environmental stimulus, a timer, or a remote control. In some embodiments of any of the aspects, following step (a), the drug delivery device adheres to the intestinal mucosa. In some embodiments of any of the aspects, the method further comprises (c) delivering the active agent to the intestinal mucosa, wherein step (c) occurs simultaneously with step (b). In some embodiments of any of the aspects, the method further comprises, after step (c), releasing the drug delivery device from the intestinal mucosa. In some embodiments of any of the aspects, the drug delivery device is released by disintegration, loss of adhesion to the intestinal mucosa, or a combination thereof.

In one aspect of any of the embodiments, described herein is an iontophoretic device comprising at least two electrodes and an active agent. In one aspect of any of the embodiments, described herein is an intestinal or oral iontophoretic device comprising at least two electrodes and an active agent.

In some embodiments of any of the aspects, iontophoresis is performed for a period of time and at an electrical current that is effective to improve permeability of a therapeutic agent across the intestine compared to orally administering the same drug delivery device in the absence of iontophoresis. In some embodiments of any of the aspects, the electrical current for iontophoresis is in a range from 20 to 25 µA, from 20 to 30 µA, from 25 to 30 µA, from 30 to 35 µA, from 35 to 40 µA, from 40 to 45 µA, from 40 to 55 µA, from 45 to 55 µA, from 45 to 50 µA, from 50 to 55 µA, or from 55 to 60 µA. In some embodiments of any of the aspects, the iontophoresis is provided or performed in one or more cycles of iontophoresis, optionally wherein a cycle comprises delivering electrical current for a period of time ranging from 0.5 to 20 minutes followed by a recovery time period ranging from 0.5 to 20 minutes. In some embodiments of any of the aspects, the iontophoresis is provided or performed in one or more cycles of iontophoresis, optionally wherein a cycle comprises delivering electrical current for a period of time ranging from 0.5 to 15 minutes followed by a recovery time period ranging from 0.5 to 15 minutes. In some embodiments of any of the aspects, the iontophoresis is provided or performed in one or more cycles of iontophoresis, optionally wherein a cycle comprises delivering electrical current for a period of time ranging from 0.5 to 10 minutes followed by a recovery time period ranging from 0.5 to 15 minutes. In some embodiments of any of the aspects, iontophoresis, or the cycles of iontophoresis, is provided or performed for longer than one hour and less than 24 hours. In some embodiments of any of the aspects, iontophoresis, or the cycles of iontophoresis, is provided or performed for longer than 30 minutes and less than 24 hours.

In some embodiments of any of the aspects, the active agent is not released from the device before iontophoresis begins. In some embodiments of any of the aspects, the active agent is released from the device after iontophoresis begins. In some embodiments of any of the aspects, the active agent is released from the device at least 10 minutes after iontophoresis begins.

In some embodiments of any of the aspects, at least two electrodes attach to a wall of the intestine, following step (a). In some embodiments of any of the aspects, a biocompatible protective coating is released from the drug delivery device to uncover the electrodes, e.g., prior to step (b). In some embodiments of any of the aspects, the device comprises a biocompatible protective coating which covers at least two electrodes. In some embodiments of any of the aspects, the biocompatible protective coating is an enteric coating that dissolves or degrades before or upon reaching the intestine. In some embodiments of any of the aspects, the at least two electrodes extends in opposite directions from the capsule.

In some embodiments of any of the aspects, the device further comprises a mucoadhesive patch. In some embodiments of any of the aspects, the mucoadhesive patch comprises the active agent. In some embodiments of any of the aspects, the device further comprises a power supply. In some embodiments of any of the aspects, the power supply is a chip battery. In some embodiments of any of the aspects, the device further comprises an electrical circuit that connects the power supply to the electrodes. In some embodiments of any of the aspects, the power supply is attached to the electrodes through a flexible, coated electrically conductive material. In some embodiments of any of the aspects, the device further comprises a drug release trigger. In some embodiments of any of the aspects, the drug release trigger is a timer, a pH or temperature sensor, a wireless receiving module, or a combination thereof.

In some embodiments of any of the aspects, the device or patch further comprises one or more compartments, wherein at least one compartment is a reservoir comprising the active agent. In some embodiments of any of the aspects, at least one compartment is a mucoadhesive compartment. In some embodiments of any of the aspects, the device further comprises a capsule, wherein the mucoadhesive patch is inside the capsule. In some embodiments of any of the aspects, the device further comprises a microsensor, microactuator, microelectronics, or a combination thereof. In some embodiments of any of the aspects, the device further comprises the electrodes are at least 0.5 cm, 1 cm, 2 cm, 3 cm, 4 cm, or 5 cm apart from each other. In some embodiments of any of the aspects, the device or patch further comprises one or more compartments, wherein at least one compartment comprises the patch. In some embodiments of any of the aspects, at least one compartment comprises the power supply. In some embodiments of any of the aspects, the device, patch, or capsule is enterically coated. In some embodiments of any of the aspects, the device further comprises a transmitter which can transmit on or more of: location information, time of the start of drug release, elapsed time of drug release, drug release duration, remaining drug dosage, and iontophoresis activity.

In some embodiments of any of the aspects, administering the oral drug delivery device improves transport and bioavailability of the active agent.

In some embodiments of any of the aspects, the active agent is a small molecule or macromolecule. In some embodiments of any of the aspects, the active agent is administered or present in the device in an effective amount to treat one or more symptoms in the subject in need of treatment. In some embodiments of any of the aspects, the subject has type 1 or type 2 diabetes. In some embodiments of any of the aspects, the active agent is administered in an effective amount to reduce blood glucose levels. In some embodiments of any of the aspects, the active agent is insulin or an analog thereof. In some embodiments of any of the aspects, the active agent is administered or present in the device at a dosage of from 1 U/kg to 100 U/kg. In some embodiments of any of the aspects, the active agent is administered or present in the device at a dosage of from 40 U/kg to 60 U/kg. In some embodiments of any of the aspects, the active agent is administered or present in the device at a dosage of 50 U/kg.

In one aspect of any of the embodiments, described herein is a system for oral drug delivery of an active agent to a subject in need thereof comprising: a) a control unit; and b) an iontophoretic device as described herein, e.g., an oral or intestinal iontophoretic device as described herein.

In some embodiments of any of the aspects, the control unit is external. In some embodiments of any of the aspects, the external control unit is internal. In some embodiments of any of the aspects, the control unit is in electrical communication with the oral drug delivery device. In some embodiments of any of the aspects, the external control unit is a remote control. In some embodiments of any of the aspects, the remote control is configured to switch control the drug delivery device, such as by switching it on and off. In some embodiments of any of the aspects, the remote control is configured to trigger iontophoresis, release of the active agent, release of the drug delivery device from the intestinal mucosa, or a combination thereof. In some embodiments of any of the aspects, the remote control is configured to modify iontophoresis parameters. In some embodiments of any of the aspects, the external control unit comprises a power supply. In some embodiments of any of the aspects, the power supply comprises an external battery.

BRIEF DESCRIPTION OF THE DRAWINGS

FIGS. 13A-13B are illustrations of a flexible multicompartmental mucoadhesive patch 510 with two electrodes 120a, 120b. The mucoadhesive patch 510 is sufficiently flexible to be rolled inside a capsule 520 (FIG. 13A), and to open up and attach to the intestinal mucosa 540 (FIG. 13B), following release from the capsule.

FIG. 14A is a schematic comparing oral insulin delivery through intestinal wall using insulin patches alone and insulin patches with iontophoresis. The thin, dashed arrow indicates decreased amounts of insulin permeating through the intestine compared to the thick arrow, which indicates greater amounts of insulin permeating through the intestine when ionotophoresis is applied to the patches. The device is an exemplary oral drug delivery device 100 (FIG. 14A). FIG. 14B depicts blood glucose levels decreasing more quickly when patches subject to iontophoresis are applied to the intestine compared to the same patches applied to the intestine without the application of iontophoresis.

DETAILED DESCRIPTION OF THE INVENTION

Figure 1:
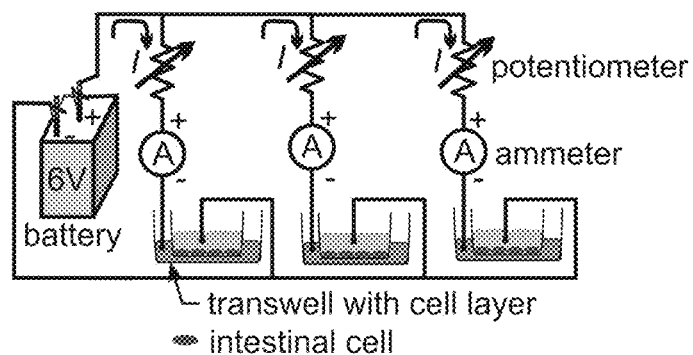
FIG. 1 is a schematic of the circuit set up used in the Example 1 in vitro iontophoresis study.

In some aspects of any of the embodiments, systems for oral drug delivery of an active agent to a subject in need thereof are described herein. Embodiments of the devices described herein are referred to variously as "oral drug delivery device", "drug delivery device" and "iontophoretic drug delivery device." Oral drug delivery devices are devices as described herein suitable for or intended for oral administration to a subject. Iontophoretic drug delivery devices are devices as described herein that can deliver an electric current to a surface or tissue in contact with one or more electrodes of the device. A device can be both oral and iontophoretic in nature. "Drug delivery device" encompasses all embodiments of the devices described herein.

In some embodiments of any of the aspects, the systems typically contain a drug delivery device (e.g., an oral and/or iontophoretic drug delivery device) and a control unit. The control unit can be external to the drug delivery device, or it can be a component in the drug delivery device. In some embodiments of any of the aspects, the control unit can control the rate and electrical current for iontophoresis.

An oral drug delivery device typically contains an active agent to be delivered and at least two electrodes. The system optionally contains a drug release trigger.

In some embodiments of any of the aspects, the oral drug delivery system can be a micro-electro-mechanical system (MEMS)-based device or a microneedle device. The system optionally contains microelectronics, such as microsensors, microactuators, or a combination thereof. In some embodiments of any of the aspects, microsensors can be used to trigger microactuators to activate iontophoresis, release the active agent, and/or release the device to after drug delivery.

An drug delivery device (e.g., an oral and/or iontophoretic drug delivery device) can have any suitable geometry and structure that allows it to be swallowed by the subject and delivered to the desired mucosal surface, such as mucosa of the intestine. Typical size ranges for the oral drug delivery device range from about 1 mm to about 20 mm, from about 1 mm to about 15 mm, from about 5 mm to about 20 mm, from about 5 mm to about 15 mm, or from about 1 mm to about 10 mm.

The drug delivery device can be hollow prior to being loaded with the active agent. For example, the device containing the active agent can be in the form of a capsule. The device can be formed of any biocompatible material suitable for oral delivery and optionally has a coating. Typically the device is formed from a material that is hydrolytically and/or enzymatically degradable.

A biocompatible material refers to materials which do not have toxic or injurious effects on biological functions. Biocompatible materials, e.g., biocompatible polymers include natural or synthetic materials. Examples of biocompatible polymers include, but are not limited to, collagen, poly(alpha esters) such as poly(lactate acid), poly(glycolic acid), polyorthoesters and polyanhydrides and their copolymers, polyglycolic acid and polyglactin, cellulose ether, cellulose, cellulosic ester, fluorinated polyethylene, phenolic, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde, polyglactin, or copolymers or physical blends of these materials.

In some embodiments, the device and/or the coating of the device can be an enteric material, e.g., a material that dissolves or degrades after passing through the stomach. Such material are well known in the art and include, but are not limited to, methyl acrylate-methacrylic acid copolymers; cellulose acetate phthalate (CAP); cellulose acetate succinate; hydroxypropyl methyl cellulose phthalate; hydroxypropyl methyl cellulose acetate succinate (hypromellose acetate succinate); polyvinyl acetate phthalate (PVAP); methyl methacrylate-methacrylic acid copolymers; shellac; cellulose acetate trimellitate; sodium alginate; zein; and an enteric coating aqueous solution comprising ethylcellulose, medium chain triglycerides [coconut], oleic acid, sodium alginate, and stearic acid. In some embodiments of any of the aspects, the coating (e.g., enteric coating) is non-conductive.

The drug delivery device can contain two or more compartments inside the device. Drug compartment(s) form may be prepared using the same material as the drug delivery device or using other hydrolytically and/or enzymatically degradable and pharmaceutically acceptable materials. Pharmaceutically acceptable materials are considered safe and effective to be administered to an individual without causing undesirable biological side effects or unwanted interactions. Typically, the drug delivery device is formed from materials that dissolve or otherwise release the active agents therein at a pH of greater than 4.0 and up to a pH of about 7.4, optionally at a pH in the range of about 4.0 to about 7.0, about 4.5 to about 6.5, about 5.0 to about 7.0, about 5.0 to about 7.4, about 5.5 to about 7.4, about 5.5 to about 7.0, about 6.0 to about 7.4, or about 6.5 to about 7.0. Preferably, the oral drug delivery device does not release the active agent at acidic pHs of 4.0 or lower.

The material forming the device and/or one dividing the inside of the device into two or more compartments may be a polymeric material. Examples of suitable biodegradable polymers include polymers of hydroxy acids such as lactic acid and glycolic acid, and copolymers with PEG, polyanhydrides, poly(ortho)esters, polyurethanes, poly(butyric acid), poly(valeric acid), poly(lactide-co-caprolactone), blends and copolymers thereof.

The oral drug delivery devices may be coated with sugars, enteric polymers or gelatin to alter dissolution of the device. Premature dissolution of the device in the mouth may be prevented by coating with hydrophilic polymers, such as hydroxypropylmethylcellulose or gelatin, resulting in dissolution in the stomach.

In some embodiments of any of the aspects, the devices described herein comprise at least two electrodes. The electrodes permit the device to apply an electrical current to a biological tissue, i.e. cause or provide iontophoresis, which improves drug delivery in the intestine as described herein. Two electrodes of opposite charge, such as a first electrode that is positively charged and a second electrode that is negatively charged, can extend through the outer surface of the oral drug delivery device. Alternatively, the electrodes can be inside the capsule, and released from the capsule following delivery into the desired site in the gastrointestinal tract. In a further alternative, the electrodes can be located inside of an enteric coating and are exposed as the enteric coating dissolves or degrades. The electrodes are located at a suitable distance from each other to prevent a short circuit.

The electrodes can be in direct contact with, e.g. adjacent to, the outer surface of the capsule or can extend beyond the outer surface of the oral dosage form, such as via a flexible, coated electrically conductive material.

The device optionally contains a power source, e.g., for delivering electrical current to the desired mucosal surface. The power source can be inside the capsule.

The drug delivery device contains one or more active agents for delivery to a subject. Active agents may be located in a drug reservoir. For example, the active agent(s) maybe dispersed through the drug reservoir. The reservoir may be in the form of a patch or wafer. Optionally, the reservoir is part of a multilayer patch or wafer.

In some embodiments of any of the aspects, the drug delivery device can be in the form of, or can comprise, a hollow or partially hollow capsule. Gelatin capsules, available in sizes 000, 00, 0, 1, 2, 3, 4, and 5, from manufactures such as Capsugel®, may be modified to include the electrodes and other electronic components, described herein.

One or more active agent(s) are typically inside the capsule. The capsule may contain a drug reservoir, such as in the form of a patch, which contains the active agent(s). The patch can be a mucoadhesive patch.

The capsule typically contains two electrodes of opposite charge, such as a first electrode that is positively charged, and a second electrode that is negatively charge. The electrodes can extend through the surface of the capsule such that they are located on the outer surface of the capsule or indirectly attached to the capsule, such as via a flexible, coated electrically conductive material. The electrodes are located at a suitable distance from each other to prevent a short circuit.

Optionally, the capsule also contains a power source. The capsule can contain a coating on its outer surface, such as an enteric coating. The coating can prevent early dissolution of the capsule, such as at the highly acidic pHs of the stomach, and facilitate delivery of the device to the intestine.

Optionally, the drug delivery device includes a drug reservoir containing one or more active agents. In some embodiments of any of the aspects, following delivery of the oral dosage form to the desired site in the gastrointestinal tract, the drug reservoir is released from the device and adheres to a mucosal site, to deliver the active agents into or across the intestinal wall. The drug reservoir can be in the form of a patch, wafer, or film. The drug reservoir may be one or more layers in a multilayered patch, wafer or film.

The active agents are typically in a pharmaceutical formulation that is the form of a liquid, such as a suspension or solution in water or non-aqueous media, or in the form of a gel. Optionally, the active agent is in the form of a solid, such as a powder, tablet, or film, that dissolves or disperses in the presence of aqueous media, such as bodily fluids.

The device optionally also contains a chemical permeation enhancer (CPE). The CPE may be in the drug reservoir or in a separate compartment from the one or more active agents.

The drug reservoir can be included in a patch. The patches may be mucoadhesive. The mucoadhesive patch may have any suitable shape. The mucoadhesive patch may be a multicompartmental device that contains a mucoadhesive compartment that exhibits strong adhesion on a mucosal membrane. The mucoadhesive compartment can be backed by a drug compartment comprising a drug along with one or more suitable excipients. The drug compartment can be backed by the supporting layer.

Other orders of the layers are also suitable. For example, the order of the layers in the patch can be reversed so that the drug compartment is located between the mucoadhesive compartment and a supporting layer.

Optionally, the patch contains a mucoadhesive compartment that extends beyond the outer perimeter of the drug compartment and forms a flange. The flange forming mucoadhesive compartment can facilitate adhesion of the patch to a mucosal surface.

Optionally, the patch includes more than one compartment in which the active agent(s) or other molecules are distributed. For example, the patch can be a multicompartment patch where the drug is distributed in several compartments. Each compartment can contain the same active agent, optionally at the same or different dosages. For example, each compartment may contain different concentrations of the same active agent.

Alternatively, one or more of the compartments contains a different active agent from the active agent(s) in the remaining compartment(s). Or one or more of the compartments contain a chemical permeation enhancer, with or without the active agent(s).

The patches typically contain a drug reservoir containing the active agent(s). Optionally at least one surface of the mucoadhesive patch, but not all of the patch, is coated with a protective coating. In the portion of the surface of the mucoadhesive patch without the protective coating, the surface may be covered with a bioadhesive layer for adhering the patch to a mucosal surface. At least one side of the patch is substantially permeable, and at least another side of the patch is substantially impermeable; this directs the delivery of the active agents.

The mucoadhesive compartment or layer can contain polymers that strongly adhere to the mucus layer of intestine. Additionally, the patch can include a protective outer layer, that protects the mucosal surface to which the device adheres and biologically active agents, such as enzymes from entering the mucosal site.

Optionally, the patch or drug reservoir swells when attached to the mucosal site to facilitates concentration gradient mediated transport of the active agent(s) across the intestine.

The dimensions of the patch are suitable to fit inside the oral drug delivery device. For example, the patch includes at least one dimension between 100 micrometers and 5 millimeters and two dimensions between 100 micrometers and 5 millimeters, between 100 micrometers and 3 millimeters, or between 500 micrometers and 2 millimeters.

The patch can be sufficiently flexible to be rolled and placed within the capsule for oral drug delivery. An example of this patch is illustrated in FIGS. 13A and 13B. Rolling makes it possible to put an otherwise large patch 510 into a manageable size capsule 520 for oral drug delivery (as illustrated in FIG. 13B).

The device or patch optionally contains a mucoadhesive layer or compartment, which contains any suitable, biocompatible mucoadhesive material. Optionally, the mucoadhesive layer or compartment contains one or more of Carbopol polymer, pectin and a modified cellulose, such as Carbopol® 934 (Lubrizol Advanced Materials, Inc., pectin (Sigma Chemicals, St. Louis, MO), and sodium carboxylmethylcellulose (SCMC, Aldrich, Milwaukee, WI). The weight percent of each material in the mixture can be varied to achieve different mucoadhesive effects. For example, the weight ratio of Carbopol:pectin:SCMC can be 1:1:2.

Other suitable mucoadhesive polymers may be used and include polyanhydrides, and polymers and copolymers of acrylic acid, methacrylic acid, and their lower alkyl esters, for example polyacrylic acid, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate), carbopol, pectin, chitosan, SCMC, HPMC may also be used.

The mucoadhesive surface, layer, or compartment of the patch may further contain a targeting moiety to facilitate targeting of the agent to a specific site in vivo. The targeting moiety may be any moiety that is conventionally used to target an agent to a given in vivo site, such as an antibody, a receptor, a ligand, a peptidomimetic agent, an aptamer, a polysaccharide, a drug, or a product of phage display.

The devices, systems and methods described herein can be used to deliver any suitable active agent (also referred to herein as "drug") to a subject in need of treatment. The active agents can be a chemical or biological molecule providing a therapeutic, diagnostic, prophylactic, or nutraceutical effect in vivo. The active agent is selected based on the disease or disorder to be treated or prevented. The devices described herein can deliver and/or comprise a single active agent or a combination of two or more active agents.

As used herein, an "active compound" or "active agent" is any agent which will exert an effect on a target cell or organism. The terms "compound" and "agent" refer to any entity which is normally not present or not present at the levels being administered and/or provided to a cell, tissue or subject. An agent can be selected from a group comprising: chemicals; small organic or inorganic molecules; signaling molecules; nucleic acid sequences; nucleic acid analogues; proteins; peptides; enzymes; aptamers; peptidomimetic, peptide derivative, peptide analogs, antibodies; intrabodies; biological macromolecules, extracts made from biological materials such as bacteria, plants, fungi, or animal cells or tissues; naturally occurring or synthetic compositions or functional fragments thereof. In some embodiments, the agent is any chemical, entity or moiety, including without limitation synthetic and naturally-occurring non-proteinaceous entities. Agents can be known to have a desired activity and/or property, or can be selected from a library of diverse compounds. Non-limiting examples of active compounds contemplated for use in the methods described herein include small molecules, polypeptides, nucleic acids, chemotherapies/chemotherapeutic compounds, antibodies, antibody reagents, vaccines, a GLP-1 polypeptide or mimetic/analog thereof, and insulin. Examples of active agents include, but are not limited to, nucleic acids, nucleic acid analogs, small molecules, macromolecules, peptidomimetics, proteins, peptides, carbohydrates or sugars, lipids, or surfactants, or a combination thereof.

Suitable drugs include, but are not limited to, the following categories and examples of drugs and alternative forms of these drugs such as biologically acceptable salts, free acid forms, free base forms, and hydrates:

analgesics/antipyretics (e.g., aspirin, acetaminophen, ibuprofen, naproxen sodium, buprenorphine, propoxyphene hydrochloride, propoxyphene napsylate, meperidine hydrochloride, hydromorphone hydrochloride, morphine, oxycodone, codeine, dihydrocodeine bitartrate, pentazocine, hydrocodone bitartrate, levorphanol, diflunisal, trolamine salicylate, nalbuphine hydrochloride, mefenamic acid, butorphanol, choline salicylate, butalbital, phenyltoloxamine citrate, diphenhydramine citrate, methotrimeprazine, cinnamedrine hydrochloride, and meprobamate);

antibiotics (e.g., neomycin, streptomycin, chloramphenicol, cephalosporin, ampicillin, penicillin, tetracycline, and ciprofloxacin);

antidiabetics (e.g., biguanides and sulfonylurea derivatives);

antifungal agents (e.g., griseofulvin, ketoconazole, itraconizole, amphotericin B, nystatin, and candicidin);

antihypertensive agents (e.g., propranolol, propafenone, oxyprenolol, nifedipine, reserpine, trimethaphan, phenoxybenzamine, pargyline hydrochloride, deserpidine, diazoxide, guanethidine monosulfate, minoxidil, rescinnamine, sodium nitroprusside, rauwolfia serpentina, alseroxylon, and phentolamine);

anti-inflammatories (e.g., (non-steroidal) indomethacin, ketoprofen, flurbiprofen, naproxen, ibuprofen, ramifenazone, piroxicam, (steroidal) cortisone, dexamethasone, fluazacort, celecoxib, rofecoxib, hydrocortisone, prednisolone, and prednisone);

antineoplastics (e.g., cyclophosphamide, actinomycin, bleomycin, daunorubicin, doxorubicin, epirubicin, mitomycin, methotrexate, fluorouracil, carboplatin, carmustine (BCNU), methyl-CCNU, cisplatin, etoposide, camptothecin and derivatives thereof, phenesterine, paclitaxel and derivatives thereof, docetaxel and derivatives thereof, vinblastine, vincristine, tamoxifen, and piposulfan);

immunosuppressive agents (e.g., cyclosporine, azathioprine, mizoribine, and FK506 (tacrolimus));

antimigraine agents (e.g., ergotamine, propranolol, isometheptene mucate, and dichloralphenazone);

antianginal agents (e.g., beta-adrenergic blockers; calcium channel blockers such as nifedipine, and diltiazem; and nitrates such as nitroglycerin, isosorbide dinitrate, pentaerythritol tetranitrate, and erythrityl tetranitrate);

antiarthritic agents (e.g., phenylbutazone, sulindac, penicillamine, salsalate, piroxicam, azathioprine, indomethacin, meclofenamate, gold sodium thiomalate, ketoprofen, auranofin, aurothioglucose, and tolmetin sodium);

antigout agents (e.g., colchicine, and allopurinol);

anticoagulants (e.g., heparin, heparin sodium, and warfarin sodium);

thrombolytic agents (e.g., urokinase, streptokinase, and alteplase);

antifibrinolytic agents (e.g., aminocaproic acid);

hemorheologic agents (e.g., pentoxifylline);

antiplatelet agents (e.g., aspirin);

antihistamines/antipruritics (e.g., hydroxyzine, diphenhydramine, chlorpheniramine, brompheniramine maleate, cyproheptadine hydrochloride, terfenadine, clemastine fumarate, triprolidine, carbinoxamine, diphenylpyraline, phenindamine, azatadine, tripelennamine, dexchlorpheniramine maleate, methdilazine, and);

agents useful for calcium regulation (e.g., calcitonin, and parathyroid hormone);

antibacterial agents (e.g., amikacin sulfate, aztreonam, chloramphenicol, chloramphenicol palmitate, ciprofloxacin, clindamycin, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, and colistin sulfate);

antiviral agents (e.g., interferon alpha, beta or gamma, zidovudine, amantadine hydrochloride, ribavirin, and acyclovir);

antimicrobials (e.g., cephalosporins such as cefazolin sodium, cephradine, cefaclor, cephapirin sodium, ceftizoxime sodium, cefoperazone sodium, cefotetan disodium, cefuroxime e azotil, cefotaxime sodium, cefadroxil monohydrate, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, and cefuroxime sodium; penicillins such as ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G procaine, methicillin sodium, and nafcillin sodium; erythromycins such as erythromycin ethylsuccinate, erythromycin, erythromycin estolate, erythromycin lactobionate, erythromycin stearate, and erythromycin ethylsuccinate; and tetracyclines such as tetracycline hydrochloride, doxycycline hyclate, and minocycline hydrochloride, azithromycin, clarithromycin);

anti-infectives (e.g., GM-CSF);

steroidal compounds, hormones and hormone analogues (e.g., incretins and incretin mimetics such as GLP-1 and exenatide, androgens such as danazol, testosterone cypionate, fluoxymesterone, ethyltestosterone, testosterone enathate, methyltestosterone, and fluoxymesterone; estrogens such as estradiol, estropipate, and conjugated estrogens; progestins such as methoxyprogesterone acetate, and norethindrone acetate; corticosteroids such as triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate, methylprednisolone sodium succinate, hydrocortisone sodium succinate, triamcinolone hexacetonide, hydrocortisone, hydrocortisone cypionate, prednisolone, fludrocortisone acetate, paramethasone acetate, prednisolone tebutate, and prednisolone acetate; and thyroid hormones such as levothyroxine sodium);

hypoglycemic agents (e.g., human insulin, purified beef insulin, purified pork insulin, recombinantly produced insulin, insulin analogs, glyburide, chlorpropamide, glipizide, tolbutamide, and tolazamide);

hypolipidemic agents (e.g., clofibrate, dextrothyroxine sodium, probucol, pravastitin, atorvastatin, lovastatin, and niacin);

agents useful for erythropoiesis stimulation (e.g., erythropoietin);

oil-soluble vitamins (e.g., vitamins A, D, E, K, and the like);

as well as other drugs such as mitotane, halonitrosoureas, anthrocyclines, and ellipticine.

The active agent can be a peptide or protein. Proteins are polymers containing amino acids linked to each other by peptide bonds to form a polypeptide for which the chain length is sufficient to produce at least a detectable tertiary structure. Proteins having a molecular weight greater than about 100 kDa may be designated "high-molecular-weight proteins," whereas proteins having a molecular weight less than about 100 kDa may be designated "low-molecular-weight proteins." The term "low-molecular-weight protein" excludes small peptides lacking the requisite of at least tertiary structure necessary to be considered a protein. Protein molecular weight may be determined using standard methods known to one skilled in the art, including, but not limited to, mass spectrometry (e.g., ESI, MALDI) or calculation from known amino acid sequences and glycosylation. Proteins can be naturally occurring or non-naturally occurring, synthetic, or semi-synthetic.

As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

In some embodiments of any of the aspects, the active compound can be a therapeutic compound or drug, e.g., an agent or compound which is therapeutically effective for the treatment of at least one condition in a subject. Therapeutic compounds are known in the art for a variety of conditions, see, e.g., the database available on the world wide web at drugs.com or the catalog of FDA-approved compounds available on the world wide web at catalog.data.gov/dataset/drugsfda-database; each of which is incorporated by reference herein in its entirety.

For example, the active agent can be insulin or an analog thereof. An insulin analog is an altered insulin, different from the insulin secreted by the pancreas, but still available to the body for performing the same action as natural insulin. Through genetic engineering of the underlying DNA, the amino acid sequence of insulin can be changed to alter its ADME (absorption, distribution, metabolism, and excretion) characteristics. Examples include insulin lispro, insulin glargine, insulin aspart, insulin glulisine, and insulin detemir, and blends and combinations thereof. The insulin can also be modified chemically, for example, by acetylation. Human insulin analogs are altered human insulin that is able to perform the same action as human insulin.

Glucagon-Like Peptide-1(GLP-1), is known to reduce food intake and hunger feelings in humans and is an incretin derived from the transcription product of the proglucagon gene that contributes to glucose homeostasis. GLP-1 mimetics are currently being used in the treatment of Type 2 diabetes. Recent clinical trials have shown that these treatments not only improve glucose homeostasis but also succeed in inducing weight loss. As used herein. "GLP-1 polypeptide" refers to the various pre- and pro-peptides and cleavage products of GLP-1, e.g., for human: GLP-1(1-37) (SEQ ID NO: 2), GLP-1 (7-36) (SEQ ID NO: 3), and GLP-1 (7-37) (SEQ ID NO: 4). In some embodiments, a GLP-1 polypeptide can be GLP-1 (7-36) and/or GLP-1 (7-37) or the correlating polypeptides from a species other than human. Sequences for GLP-1 polypeptides are known in the art for a number of species, e.g. human GLP-1 (NCBI Gene ID: 2641) polypeptides (e.g., NCBI Ref Seq: NP_002045.1; SEQ ID NO: 1) and SEQ ID NOs: 2-4. In some embodiments, a pre or pro-peptide of GLP-1 can be used in the methods or compositions described herein, e.g., a glucagon preproprotein (e.g., SEQ ID NO: 1). Naturally-occurring alleles or variants of any of the polypeptides described herein are also specifically contemplated for use in the methods and compositions described herein.

```
                                                              SEQ ID NO: 1
  1 mksiyfvagl fvmlvqgswq rslqdteeks rsfsasqadp lsdpdqmned krhsqgtfts 61 dyskyldsrr aqdfvqwlmn tkrnrnniak rhdeferhae gtftsdvssy legqaakefi 121 awlvkgrgrr dfpeevaive elgrrhadgs fsdemntild nlaardfinw liqtkitdrk SEQ ID NO: 2
    hdeferhae gtftsdvssy legqaakefi awlvkgrg SEQ ID NO: 3
    hae gtftsdvssy legqaakefi awlvkgr SEQ ID NO: 4
    hae gtftsdvssy legqaakefi awlvkgrg
```

Various GLP-1 mimetics are known in the art and used in the treatment of diabetes. GLP-1 mimetics (or analogues) can include exendin-4 (a Heloderma lizard polypeptide with homology to human GLP-1) and derivatives thereof, GLP-1 analogs modified to be DPP-IV resistant, or human GLP-1 polypeptides conjugated to various further agents, e.g., to extend the half-life. GLP-1 mimetics/analogues can include, e.g., exenatide, lixisenatide, dulaglutide, semaglutide, albiglutide, LY2189265, liraglutide, and taspoglutide. Examples of such molecules and further discussion of their manufacture and activity can be found in the art, e.g., Gupta. Indian J. Endocrinol Metab 17:413-421 (2013); Garber. Diabetes Treatments 41:S279-S284 (2018); US Patent Publication US2009/0181912; and International Patent Publication WO2011/080103, each of which is incorporated by reference herein in its entirety.

In some embodiments of any of the aspects, the active agent is administered or present in the device at a dosage of from 1 U/kg to 100 U/kg, from 40 U/kg to 60 U/kg, or at a dosage of 50 U/kg. In some embodiments of any of the aspects, the active agent is insulin or an analog thereof and is administered or present in the device at a dosage of from 1 U/kg to 100 U/kg, from 40 U/kg to 60 U/kg, or at a dosage of 50 U/kg.

In some embodiments of any of the aspects, the at least one active agent is at a dose of from about 1.0-40.0 mg/kg. In some embodiments of any of the aspects, the at least one active agent is at a dose of from 1.0-40.0 mg/kg. In some embodiments of any of the aspects, the at least one active agent is at a dose of from about 1.0-20.0 mg/kg. In some embodiments of any of the aspects, the at least one active agent is at a dose of from 1.0-20.0 mg/kg.

A description of these and other classes of useful drugs and a listing of species within each class can be found in Martindale, *The Extra Pharmacopoeia, 30th Ed.* (The Pharmaceutical Press, London 1993), the disclosure of which is incorporated herein by reference in its entirety.

The active agents described herein can be formulated into pharmaceutical formulations composed of one or more of the active agents in association with a pharmaceutically acceptable carrier. See, e.g., *Remington's Pharmaceutical Sciences*, latest edition, by E.W. Martin Mack Pub. Co., Easton, PA, which discloses typical carriers and conventional methods of preparing pharmaceutical formulations that can be used in conjunction with the active agents described herein and which is incorporated by reference herein. These are typically standard carriers for administration of compositions to humans, such as sterile water, saline, and buffered solutions at physiological pH.

The active agents can be included in a pharmaceutical formulation, which is delivered by the devices and systems described herein. The pharmaceutical formulation can also include one or more carriers, thickeners, diluents, buffers, preservatives, emulsifiers, dispersing aids, binders, surface active agents, or a combination thereof. Preservatives and other additives can also be present such as, for example, antimicrobials, anti-oxidants, chelating agents, and inert gases and the like.

Pharmaceutical formulations can also include one or more additional active agents such as antimicrobial agents, anti-inflammatory agents, anesthetics, and the like. Optionally, the additional active agent is included in a separate compartment or portion of the device.

The devices, systems and methods described herein can be used to deliver an effective amount of an active agent to treat a subject in need thereof. An effective amount of an active agent is a sufficient amount of the active agent to provide the desired result. The exact amount required varies from subject to subject, depending on the species, age, and general condition of the subject, the severity of the disease that is being treated, the particular compound used, and the like. However, an appropriate effective amount can be determined by one of ordinary skill in the art.

The dose and schedule of doses can be varied, as needed, to achieve the desired result. For example, in the treatment of a subject with type 1 or type 2 diabetes, an effective amount of an active agent, such as insulin, is effective to reduce blood glucose levels.

The drug delivery device or system typically includes or is in electrical communication with a power supply. The power supply can be an external power supply or an internal power supply, such as a battery or capacitor. The battery can be a chip battery.

When the power supply is internal to the drug delivery device, it can be located inside the drug reservoir compartment or in a separate compartment in the device. The power supply can be included in an electrical circuit in the film, tablet, patch or wafer. The power supply also is in electrical communication with each of the electrodes, such as through a flexible, coated electrically conductive material.

The drug delivery device or system (e.g., ionotophoretic drug delivery device) includes two or more electrodes that can be placed in contact with and adhere to the intestinal mucosa. The electrodes are partially coated with an insulating material, such as polyimide and glass. The electrodes can be made from any suitable conductive materials including aluminum, platinum, gold, copper, lead, zinc, and silver. The insulating and conducting properties of the materials in the electrodes or in electrical communication therewith can be specified by their electrical conductivities. For insulators (or dielectric materials), the conductivity ($\sigma$) is generally to be lower than $10^{-8}$ S/m; while the conductivity is generally larger than $10^6$ S/m for conducting materials (R. A. Higgins, *Materials for engineers and technicians*. (Routledge, 2010)).

The electrodes are located at a suitable distance from each other, and optionally can contact the surface of the capsule, to prevent a short circuit. For example, the electrodes can be 0.5 cm-5 cm apart from each other, such as 0.5-1 cm, 1-2 cm, 2-3 cm, 4-5 cm, optionally at least 0.5 cm, 1 cm, 2 cm, 3 cm, 4 cm, or 5 cm apart from each other, or even farther apart.

The electrodes are in electrical communication with a power supply allowing them to transmit electrical current between the two electrodes, when they are applied onto the mucosal surface. A sufficient amount of current is applied to the surface for a sufficient time period to facilitate transport of the active agent(s).

The oral delivery device has a sufficient surface area to cover the electrodes when they are attached to the mucosal surface.

The electrodes can be directly or indirectly attached to the outer surface of the capsule.

Optionally, a first electrode is located on a first side or end of the device and at least a second electrode is located on a second side or end of the device, where the first and second sides or ends are opposite each other.

The electrodes can be attached to the power supply through the surface of the capsule via a flexible, coated electrically conductive material, preferably the material is coated with an insulting material.

The electrodes can also attach directly or indirectly to the drug reservoir inside the capsule. The electrodes can be in physical contact with the drug reservoir inside the capsule.

The electrodes are typically partially coated with a mucoadhesive layer to attach to a mucosal surface.

Each electrode is optionally coated with a mucoadhesive layer at its distal end, which contains any suitable, biocompatible mucoadhesive material. Optionally, the mucoadhesive layer or compartment contains one or more of Carbopol polymer, pectin and a modified cellulose, such as Carbopol® 934 (Lubrizol Advanced Materials, Inc., pectin (Sigma Chemicals, St. Louis, MO), and sodium carboxylmethylcellulose (SCMC, Aldrich, Milwaukee, WI). The weight percent of each material in the mixture can be varied to achieve different mucoadhesive effects. For example, the weight ratio of Carbopol:pectin:SCMC can be 1:1:2.

Other suitable mucoadhesive polymers may be used and include, polyanhydrides, and polymers and copolymers of acrylic acid, methacrylic acid, and their lower alkyl esters, for example polyacrylic acid, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate), carbopol, pectin, chitosan, SCMC, HPMC may also be used.

In use, the electrodes are optionally covered with a protective coating. The protective coating has a sufficient surface area to cover the electrodes during the application of iontophoresis. The protective coating is made of inert biocompatible material such as a polymer containing polyethylene glycol chains. The protective coating can be part of the drug delivery device, and is optionally the outer layer or coating on the drug delivery device. The protective coating can be released, dissolved, or degraded in order to uncover the electrodes. In some embodiments of any of the aspects, the protective coating is an enteric coating as described elsewhere herein.

The system can contain one or more electrical circuits. The electrical circuits can include a power supply, a conducting path, and at least two electrodes. Optionally, the electrical circuits also contain a switch to control the current flow.

The electrical circuits can be located in a drug reservoir or drug-containing layer of a patch or film. The electrical circuits or potions thereof can be located within a compartment of the capsule.

Optional elements of the device or system can include a) a control unit, b) a drug release trigger, c) a carrier, d) excipient, e) a chemical penetration enhancer, f) an iontophoresis release trigger, and/or g) a transmitter.

In some embodiments of any of the aspects, the control unit is an external control unit. The external control unit can be a remote control, optionally with a power supply or in electrical communication with a power supply. The remote control can switch the drug delivery device on/off. Optionally, the remote control can guide the drug delivery device to a desired location in the patient's body following oral administration.

The remote control can also trigger iontophoresis and/or control iontophoresis parameters, such as the electrical current range or the period time for application of the electrical current.

The remote control can also trigger release of the active agent, and/or release of the drug delivery device from the intestinal mucosa.

The power supply for the remote control can be a battery or plug into a supply of electricity.

In some embodiments of any of the aspects, the control unit is an internal control unit. The internal control unit is delivered to the patient, and typically is inside an oral drug delivery device. The internal control system can perform the same functions as described above with respect to the remote control.

In some embodiments of any of the aspects, any of the control units described herein can relate to systems (and computer readable media for causing computer systems) for obtaining, retrieving, or sending data or a mechanical and/or electrical signal. Control units can optionally comprise one or more of sensors, batteries, triggers, a storage module configured to store data output from the device, and a display module for displaying a content based in part on the data output from the device. A control unit can comprise at least one memory containing at least one computer program adapted to control the operation of the device as described herein and/or a storage module configured to store output data from the device.

The term "computer" can refer to any non-human apparatus that is capable of accepting a structured input, processing the structured input according to prescribed rules, and producing results of the processing as output. Examples of a computer include: a computer; a general purpose computer; a supercomputer; a mainframe; a super mini-computer; a mini-computer; a workstation; a micro-computer; a server; an interactive television; a hybrid combination of a computer and an interactive television; a tablet; a smartphone; and application-specific hardware to emulate a computer and/or software. A computer can have a single processor or multiple processors, which can operate in parallel and/or not in parallel. A computer also refers to two or more computers connected together via a network for transmitting or receiving information between the computers. An example of such a computer includes a distributed computer system for processing information via computers linked by a network.

The term "computer-readable medium" may refer to any storage device used for storing data accessible by a computer, as well as any other means for providing access to data by a computer. Examples of a storage-device-type computer-readable medium include: a magnetic hard disk; a floppy disk; an optical disk, such as a CD-ROM and a DVD; a magnetic tape; a memory chip. The term a "computer system" may refer to a system having a computer, where the computer comprises a computer-readable medium embodying software to operate the computer. The term "software" is used interchangeably herein with "program" and refers to prescribed rules to operate a computer. Examples of software include: software; code segments; instructions; computer programs; and programmed logic.

The computer readable storage media can be any available tangible media that can be accessed by a computer. Computer readable storage media includes volatile and nonvolatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and nonvolatile memory, and any other tangible medium which can be used to store the desired information and which can accessed by a computer including and any suitable combination of the foregoing.

Computer-readable data embodied on one or more computer-readable media may define instructions, for example, as part of one or more programs that, as a result of being executed by a computer, instruct the computer to perform one or more of the functions described herein, and/or various embodiments, variations and combinations thereof. Such instructions may be written in any of a plurality of programming languages, for example, Java, J #, Visual Basic, C, C #, C++, Fortran, Pascal, Eiffel, Basic, COBOL assembly language, R, SAS, and the like, or any of a variety of combinations thereof. The computer-readable media on which such instructions are embodied may reside on one or more of the components of either of a system, or a computer readable storage medium described herein, may be distributed across one or more of such components.

The computer-readable media may be transportable such that the instructions stored thereon can be loaded onto any computer resource to implement the aspects of the present methods, devices, and systems discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a computer to implement aspects of the present invention. The computer executable instructions may be written in a suitable computer language or combination of several languages.

Embodiments of the invention can be described through functional modules, which are defined by computer executable instructions recorded on computer readable media and which cause a computer to perform method steps when executed. The modules are segregated by function for the sake of clarity. However, it should be understood that the modules/systems need not correspond to discreet blocks of code and the described functions can be carried out by the execution of various code portions stored on various media and executed at various times. Furthermore, it should be appreciated that the modules can perform other functions, thus the modules are not limited to having any particular functions or set of functions. The functional modules can be executed on one, or multiple, computers, or by using one, or multiple, computer networks. The measuring module has computer executable instructions to provide e.g., levels of expression products etc in computer readable form.

The internal control system can include a power supply and a mechanism to control or trigger release of the drug delivery device from the capsule, to control iontophoresis, to control drug release, and/or to trigger release of the drug delivery device from the intestinal mucosa.

The release of the active agent or pharmaceutical formulation from the drug delivery device can be triggered by an environmental stimulus such as pH, temperature, ionic strength, mechanical strength, magnetic/electric fields, ultrasound, and/or light. The release of the active agent of pharmaceutical formulation from the drug delivery device can occur upon dissolution of the drug reservoir compartment. Optionally, the device includes a timer or an internal control system, or a combination thereof, or is in communication with a remote control to control or trigger release of the active agent from the device.

For example, an oral drug delivery device, such as a patch, may be released from the device, and adhere at a site on the intestinal walls. The active agent then is released from the patch and into the intestine. For example, the active agent could be released into the intestinal wall when the drug reservoir dissolves. Alternatively, the device can open a compartment, valve, or reservoir, or actuate a microneedle device or the like upon a signal from an electronic drug release trigger. Such an electronic drug release can comprise a timer, a pH or temperature sensor, or a wireless receiving module that receives a signal from an external control system. Such a signal from an external control system can be sent by a computer system on the basis of elapsed time, location of the drug delivery device, pH or temperature readings, or the like. Alternatively such a signal from an external control system can be sent upon human user input.

A drug delivery device described herein can also comprise an iontophoresis control trigger that provides electrical current to the electrodes, or, e.g., opens a compartment comprising one or more electrodes upon receiving a signal from the iontphoresis release trigger. Such an electronic release can comprise a timer, a pH or temperature sensor, or a wireless receiving module that receives a signal from an external control system. Such a signal from an external control system can be sent by a computer system on the basis of elapsed time, location of the drug delivery device, pH or temperature readings, or the like. Alternatively such a signal from an external control system can be sent upon human user input.

In some embodiments, an iontophoretic control trigger is not provided, e.g., the device is powered on before oral administration and electrical power is provided continuously to the electrodes. Upon contacting a tissue, the circuit is completed and a current is provided to the tissue. Premature application of a current can be prevented by a nonconductive enteric coating covering the electrodes.

The device can optionally comprise a transmitter that sends information on one or more of location information, time of the start of drug release, elapsed time of drug release, drug release duration, remaining drug dosage, and/or iontophoresis activity. The signal can be sent, e.g., to an external control system. Such embodiments can permit the subject and/or a medical practitioner to precisely track when and where the drug was delivered.

In embodiments where the device comprises a transmitter, a control unit can comprise a receiver and/or both the device and the control unit can comprise transceivers. The transmitters and/or transceivers can be wireless.

The term "transmitter" or "wireless transmitter" refers to an electronic device which can produce and transmit an electromagnetic wave in the air. The electromagnetic wave can be a radio wave, a microwave or an infrared. In some embodiments, the transmitter can be a separate piece of electronic device, or an electronic circuit within another device. In further embodiments, the transmitter shares at least a portion of its electronic circuit another device such as a receiver.

The term "receiver" or "wireless receiver" refers to an electronic device that can receive an electromagnetic wave in the air and converts the information carried by electromagnetic wave to a usable form. The electromagnetic wave can be a radio wave, a microwave or an infrared. In some embodiments, the receiver can be a separate piece of electronic device, or an electronic circuit within another device. In further embodiments, the receiver shares at least a portion of its electronic circuit with another device such as a transmitter.

The term "transceiver" or "wireless transceiver" refers to a device comprising both a transmitter and a receiver sharing a single housing.

The device is optionally encapsulated in an enteric capsule. Optionally, the device and/or system contains a coating on its outer surface, such as an enteric coating. The enteric capsule or coating can prevent early dissolution of the capsule and facilitate delivery of the device to the intestine. The enterically coated capsules enables the drug delivery devices to bypass the harsh acidic environment of the stomach and release the drug reservoir such as patches from the capsules specifically in the intestine. The enteric coating can be a polymer coating applied to the outside of the drug formulation to protect the drug as it passed through the stomach, providing delayed release in the small intestine. The enteric capsule or coating can dissolve, disintegrate, or degrade within when exposed to pHs that are higher than the acidic environment of the stomach, such as pHs greater than 6, for example pHs of about 6.8 and 7.

Typical of enteric polymers utilizing pH as a trigger are Eudragit polymers manufactured by Rohm America: Eudragit L100-55 dissolves at pH values greater than 5.5; Eudragit L100 dissolves at pH values exceeding 6.0; Eudragit S100 dissolves at pH values exceeding 7.0. Also suitable are cellulosic enteric polymers such as cellulose acetate phthalate.

Coatings that dissolve after 3 hours when the dosage form is administered in the fed state and after 1-2 hours when the dosage form is administered in the fasted state are suitable for delivery to the small intestine. Erosion of soluble polymer layers is one means to achieve a time-triggered, enteric dissolution. Polymers such as HPMC, HPC, PVP, PVA or combinations of the above may be used as enteric coatings. Applying thicker coating weights can increase timing of the dissolution of the coating.

The drug delivery devices may include or be delivered in a pharmaceutically acceptable carrier. Pharmaceutically acceptable materials are materials which are generally recognized as safe (GRAS), and may be administered to an individual without causing undesirable biological side effects or unwanted interactions.

The active agent can be included in the drug delivery reservoir as part of a formulation and/or with one or excipients. The formulation can include pharmaceutically acceptable excipients. Suitable excipients are determined based on a number of factors, including the dosage form, desired release rate of the drug, stability of the drug to be delivered.

Excipients include, but are not limited to, polyethylene glycols, humectants, vegetable oils, medium chain mono, di and triglycerides, lecithin, waxes, hydrogenated vegetable oils, colloidal silicon dioxide, polyvinylpyrrolidone (PVP) ("povidone"), celluloses, CARBOPOL® polymers (Lubrizol Advanced Materials, Inc.) (i.e. crosslinked acrylic acid-based polymers), acrylate polymers, other hydrogel forming polymers, plasticizers, crystallization inhibitors, bulk filling agents, solubilizers, bioavailability enhancers, thickeners, flavorings, diluents, emulsifiers, dispersing aids or binders, or combinations thereof.

The drug delivery devices may contain an additional compartment comprising one or more chemical enhancers (CPEs). The device can include two or more CPEs, where the CPE's are synergistic enhancer formulations. Optionally, formulations contain one or more of sodium laureth sulfate, decyltrimethyl ammonium bromide, chembetaine, or hexylamine.

The concentration of the one or more CPEs in the device typically has a strong effect on the ability of the CPEs to increase permeability of the drug across a given mucosal surface. The concentration of the CPE is selected to fall within the enhancer's therapeutic concentration window. The therapeutic concentration corresponds with the concentrations at which the enhancer's potency is sufficiently greater than the enhancer's toxicity. The concentration of CPE in the device ranges from about 0.01% (w/v) to about 0.1% (w/v), such as from 0.01% to 0.05% (w/v), from 0.01% to 0.02% (w/v), from 0.01% to 0.03% (w/v), from 0.01% to 0.04% (w/v), or from 0.05% (w/v) to 0.1% (w/v).

Figure 8:
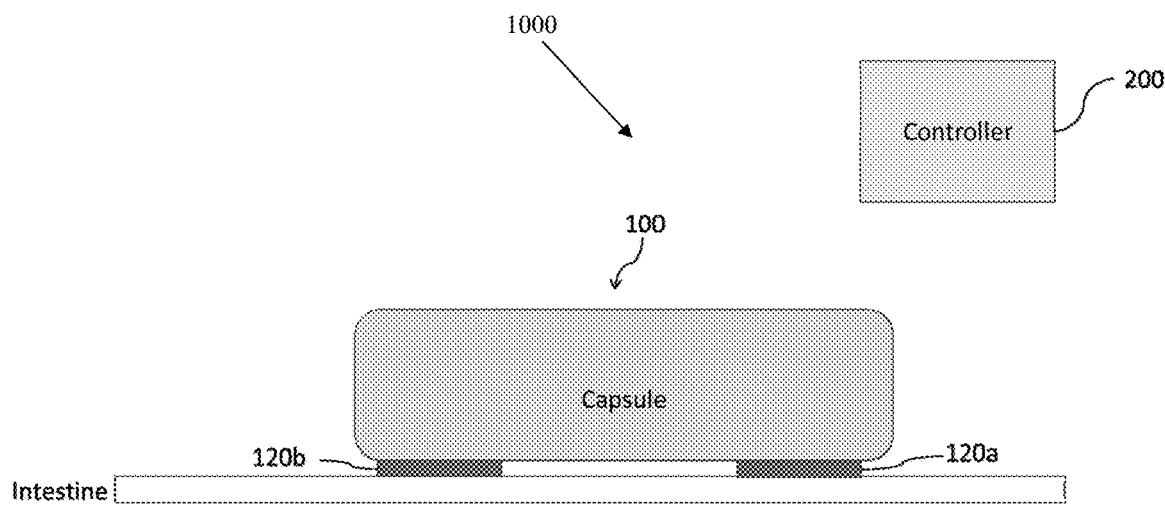
FIG. 8 is an illustration of an exemplary oral drug delivery system 1000 containing an external control unit 200 and an oral drug delivery device 100.
Figure 9:
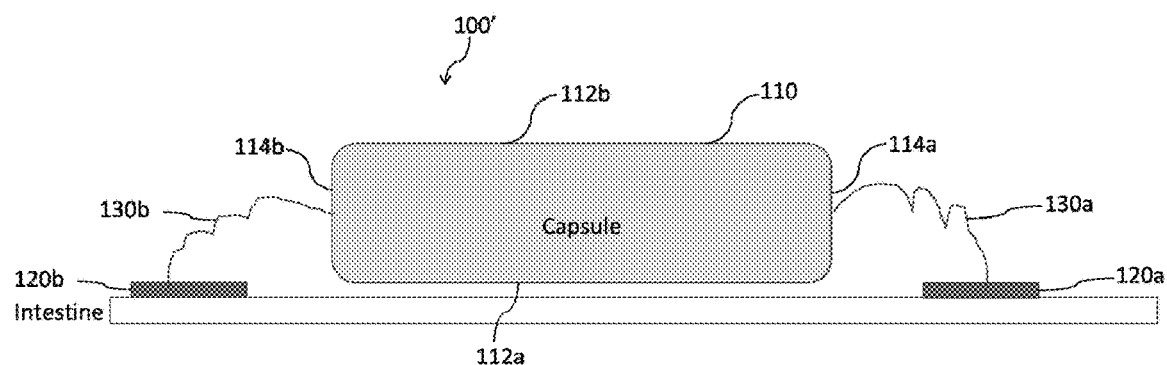
FIG. 9 is an illustration of an exemplary oral drug delivery device 100' with two electrodes 120a and 120b connected to opposite ends 114a and 114b through the outer surface 112 of the capsule 110 via flexible, coated electrically conductive connectors 130a and 130b.

A non-limiting exemplary oral drug delivery system is illustrated in FIG. 8, as illustrate in FIG. 8 the system 1000 can include an external control unit 200, electrodes 120a and 120b, and an oral drug delivery device 100. Exemplary oral drug delivery devices are illustrated in FIGS. 9-13. As shown in FIG. 9, the oral drug delivery device 100 comprises a capsule 110. Capsule 110 is attached to two electrodes 120b and 120a. The electrodes 120a and 120b are illustrated in FIG. 13A. The electrodes 120a and 120b are attached to the outer surface 112a of capsule 110 and are adjacent to each other. In some embodiments the electrodes are at least 0.5 cm, 1 cm, 2 cm, 3 cm, 4 cm, or 5 cm apart from each other. The surface 122b of the electrodes 120a and 120b is attached to capsule 110 and the surface 122a of the electrodes 120a and 120b is attached to the intestinal mucosa.

Figure 10:
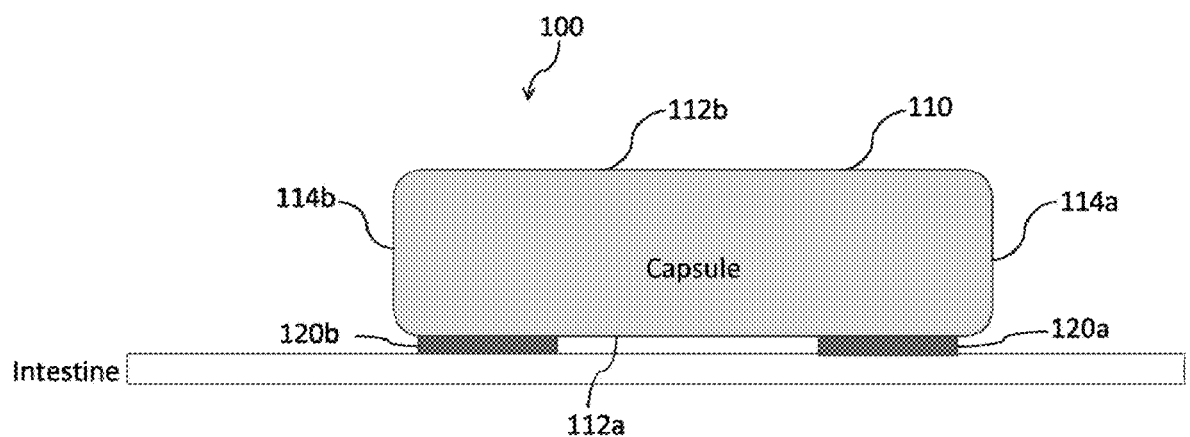
FIG. 10 is an illustration of an exemplary oral drug delivery device 100 with two electrodes 120a and 120b extending through the outer surface 112 of the capsule 110.

In some other embodiments as shown in FIG. 10, the oral drug delivery device 100' comprises a capsule 110. Capsule 110 is attached to two electrodes 120a and 120b. Each of the electrodes is attached through the outer surface 114b and 114a of the capsule 110 via a flexible, coated electrically conductive connector 130a, 130b. The surface 122a of the electrodes 120a and 120b is in contact with and adheres to the intestinal mucosa.

Figure 11:
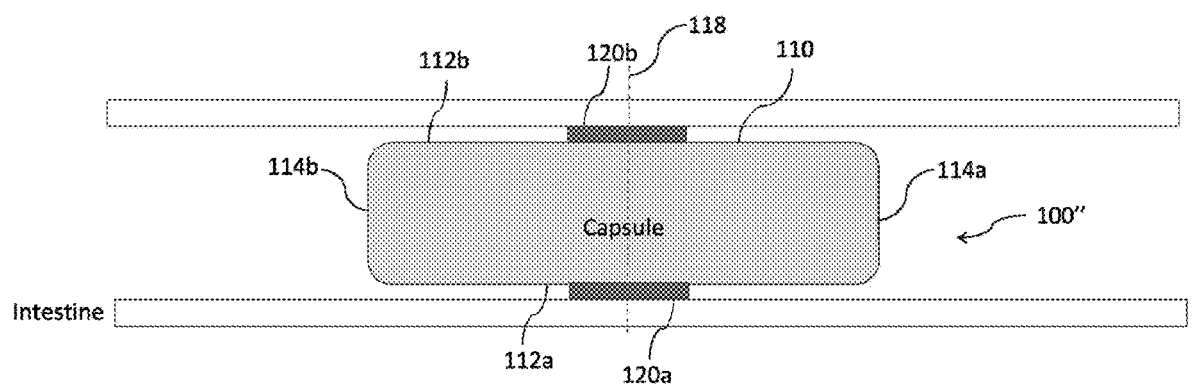
FIG. 11 is an illustration of an exemplary oral drug delivery device 100" with two electrodes 120a and 120b extending through opposite sides 114c and 114d of the outer surface 112 of the capsule 110.
Figure 12:
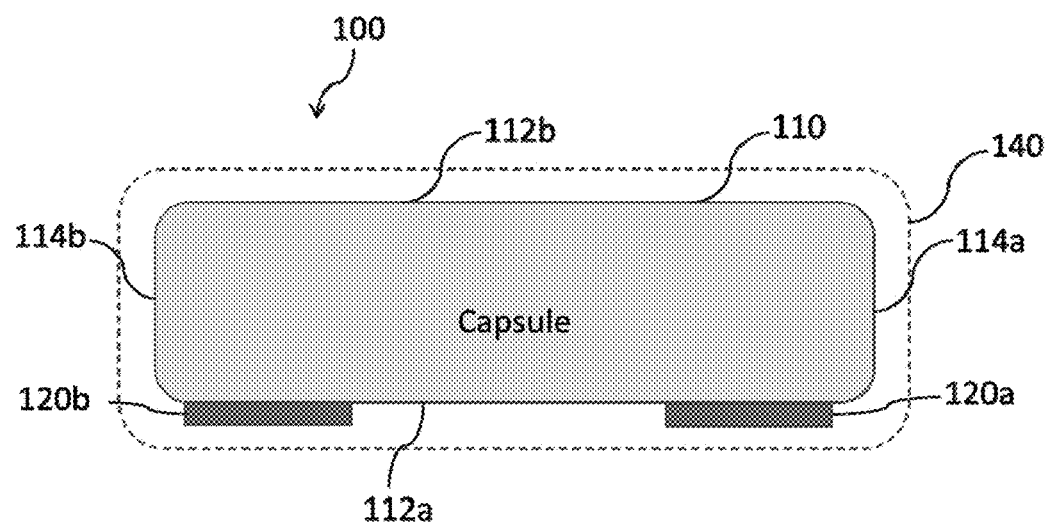
FIG. 12 is an illustration of an exemplary oral drug delivery device 100 that is enterically coated 140.
Figure 14B:
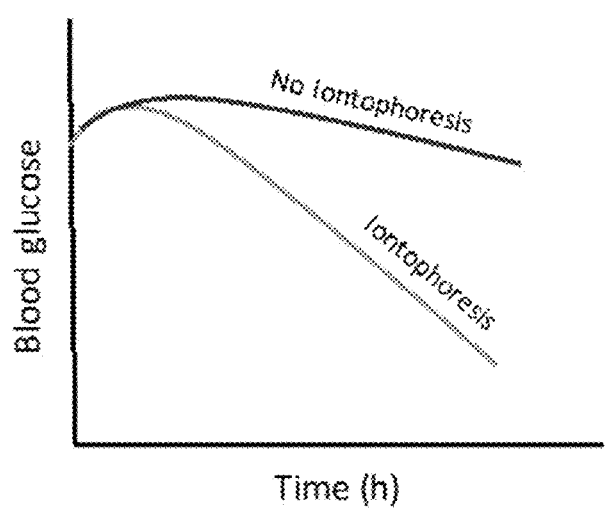
FIG. 14B is a graph, which depicts the blood glucose levels over time with and without iontophoresis.

In some other embodiments as shown in FIG. 11, the oral drug delivery device 100" comprises a capsule 110. Capsule 110 is attached to two electrodes 120a and 120b. One electrode is attached to the outer surface 112b of the capsule 110 and the other electrode is attached to the outer surface 112a of the capsule 110. In some embodiments the capsule 110 has multiple compartments 118. In some embodiments as shown in FIG. 12, the oral drug delivery devices 100, 100', or 100" are further enterically coated 140.

In some other embodiments shown in FIG. 11, the oral drug delivery device 100''' comprises a capsule 110. Capsule 110 can contain a patch, which is in physical contact with an electrode which is in electronic communication with and can be activated by a power supply.

In yet another embodiment, at least two mucoadhesive patches, each including an electrode are in electrical communication with each other to deliver iontophoresis to the desired sites.

Described herein are methods for oral drug delivery of an active agent to a subject in need thereof. The method for oral drug delivery of an active agent can include orally administering a drug delivery system to a subject and triggering iontophoresis The active agent(s) or pharmaceutical formulations described herein can be administered to the subject orally to the area to be treated. Thus, for example, an active agent(s) or pharmaceutical formulation described herein can be administered as liquids, powders or granules, suspensions or solutions in water or non-aqueous media. The active agent(s) or pharmaceutical formulations may be administered in a solid oral drug delivery device, such as described above.

In one aspect of any of the embodiments, described herein is a method for oral drug delivery of an active agent to a subject in need thereof comprising: a) orally administering an iontophoretic drug delivery device to the subject, wherein the iontophoretic drug delivery device comprises the active agent. In one aspect of any of the embodiments, described herein is a method for oral drug delivery of an active agent to a subject in need thereof comprising: a) orally administering a drug delivery device to the subject, wherein the drug delivery device comprises the active agent; and b) triggering iontophoresis.

The active agent(s) or pharmaceutical formulations may be administered, for example, in a single dosage, as a continuous dosage, one or more times daily, or less frequently, such as once a week. In certain forms, the formulations are administered orally, once daily or less frequently.

Dosage can vary, and can be administered in one or more dose administrations daily, for one or several days.

The active agent(s) or pharmaceutical formulations are administered in combination with iontophoresis in an effective amount and for an effective period of time to elicit the desired therapeutic benefit. In certain forms, the pharmaceutical formulation is administered for a period of at least one week, two weeks, three weeks, four weeks, one month, two months, three months, four months, five months, six months, seven months, eight months, nine months, ten months, eleven months, one year, or longer.

The exact amount of the formulation required will vary from subject to subject, depending on the species, age, sex, weight and general condition of the subject, extent of the disease in the subject, route of administration, whether other drugs are included in the regimen, and the like. Thus, it is not possible to specify an exact dosages for every formulation. However, an appropriate dosage can be determined by one of ordinary skill in the art using only routine experimentation. For example, effective dosages and schedules for administering the formulations in combination with iontophoresis may be determined empirically, and making such determinations is within the skill in the art.

Iontophoresis can be triggered by a variety of different stimuli, or controlled using a timer, or remote control. For example, exposure to an aqueous environment, or stimuli such as pH, temperature, ionic strength, mechanical strength, magnetic/electric fields, or light or a combination thereof. Iontophoresis is performed for a period of time and at an electrical current that is effective to improve permeability of therapeutic drugs across the intestine.

The methods include the use of iontophoresis to improve permeation of active agents across the intestinal cells to improve oral delivery of active agents. Iontophoresis is the application of external current to a surface, such as a mucosal surface.

Amongst other parameters, the efficacy of an iontophoretic therapy is greatly dependent on current density and drug concentration, indicating that any variation in these parameters may influence iontophoretic drug delivery (Dixit, et al., 2007). Iontophoresis works predominantly by establishing an electrical gradient for transport of molecules across pathways that already exist within a barrier. Oral delivery of active agents can be enhanced through iontophoresis that modulates intestinal absorptive pathways to improve permeability of such drugs across the intestine compared to oral delivery of the same active agents using the same dosage formulation in the absence of the application of iontophoresis.

Iontophoresis can be triggered by an environmental stimulus, a timer, or a remote control, as described elsewhere herein. In some embodiments of any of the aspects, the devices described herein will provide or administer iontophoresis without human intervention following oral administration. In some embodiments of any of the aspects, the devices described herein will provide or administer iontophoresis only upon receiving a signal from an external control unit, e.g., an automated signal, electronically-controlled signal, or a signal sent upon a command or input provided by a human user.

The delivery of one or more active agents is possible by using a small current gradient for short periods of time. The current gradient can be applied in a range such as 20-25 µA, 25-30 µA, 30-35 µA, 35-40 µA, 40-45 µA, 45-50 µA, 50-55 µA, or 55-60 µA.

The current density can be between 0.1 up to 10 mA/cm². Optionally, the current density can be 0.5 mA/cm². Optionally, the current density can be higher than 0.5 mA/cm². For example, the current density is in the range of 0.1-0.5 mA/cm², 0.1-0.2 mA/cm², 0.1-0.3 mA/cm², 0.1-0.4 mA/cm², 0.1-0.6 mA/cm², 0.1-0.7 mA/cm², 0.1-0.8 mA/cm², 0.1-0.9 mA/cm², 0.1-1.0 mA/cm², 0.1-2.0 mA/cm², 0.1-3.0 mA/cm², 0.1-4.0 mA/cm², 0.1-5.0 mA/cm², 0.1-6.0 mA/cm², 0.1-7.0 mA/cm², 0.1-8.0 mA/cm², 0.1-9.0 mA/cm², 0.5-1.0 mA/cm², 0.5-2.0 mA/cm², 0.5-3.0 mA/cm², 0.5-4.0 mA/cm², 0.5-5.0 mA/cm², 0.5-6.0 mA/cm², 0.5-7.0 mA/cm², 0.5-8.0 mA/cm², 0.5-9.0 mA/cm², 0.5-10.0 mA/cm², 1.0-2.0 mA/cm², 1.0-3.0 mA/cm², 1.0-4.0 mA/cm², 1.0-5.0 mA/cm², 1.0-6.0 mA/cm², 1.0-7.0 mA/cm², 1.0-8.0 mA/cm², 1.0-9.0 mA/cm², 1.0-10.0 mA/cm², 2.0-3.0 mA/cm², 2.0-4.0 mA/cm², 2.0-5.0 mA/cm², 2.0-6.0 mA/cm², 2.0-7.0 mA/cm², 2.0-8.0 mA/cm², 2.0-9.0 mA/cm², 2.0-10.0 mA/cm², 3.0-4.0 mA/cm², 3.0-5.0 mA/cm², 3.0-6.0 mA/cm², 3.0-7.0 mA/cm², 3.0-8.0 mA/cm², 3.0-9.0 mA/cm², 3.0-10.0 mA/cm², 4.0-5.0 mA/cm², 4.0-6.0 mA/cm², 4.0-7.0 mA/cm², 4.0-8.0 mA/cm², 4.0-9.0 mA/cm², 4.0-10.0 mA/cm², 5.0-6.0 mA/cm², 5.0-7.0 mA/cm², 5.0-8.0 mA/cm², 5.0-9.0 mA/cm², 5.0-10.0 mA/cm², 6.0-7.0 mA/cm², 6.0-8.0 mA/cm², 6.0-9.0 mA/cm², 6.0-10.0 mA/cm², 7.0-8.0 mA/cm², 7.0-9.0 mA/cm², 7.0-10.0 mA/cm², 8.0-9.0 mA/cm², 8.0-10.0 mA/cm², or 9.0-10.0 mA/cm². In some embodiments of any of the aspects, the electrical current for iontophoresis is in a range from 20 to 25 µA, from 20 to 30 µA, from 25 to 30 µA, from 30 to 35 µA, from 35 to 40 µA, from 40 to 45 µA, from 40 to 55 µA, from 45 to 55 µA, from 45 to 50 µA, from 50 to 55 µA, or from 55 to 60 µA.

The current can be applied to the mucosal surface in time intervals, such as current applied (on) for a first time period, followed by a recovery time (off) for a second time period. The first and second time periods can be the same or different. Optionally, the first time period (on) is shorter than the second time period (off). The sum of the first and second time periods is the time period for a single iontophoresis cycle.

For example, a cycle includes delivering electrical current for a period of time ranging from 0.5 minutes to 10 minutes, such as from 0.5 minutes, 1 minute, 1.5 minutes, 2 minutes, 2.5 minutes, 3 minutes, 3.5 minutes, 4 minutes, 4.5 minutes, 5 minutes, 5.5 minutes, 6 minutes, 6.5 minutes, 7 minutes, 7.5 minutes, 8 minutes, 8.5 minutes, 9 minutes, 9.5 minutes to 10 minutes, followed by a recovery time period ranging from 0.10 seconds to 15 minutes, optionally from 0.5 minutes, 1 minute, 1.5 minutes, 2 minutes, 2.5 minutes, 3 minutes, 3.5 minutes, 4 minutes, 4.5 minutes, 5 minutes, 5.5 minutes, 6 minutes, 6.5 minutes, 7 minutes, 7.5 minutes, 8 minutes, 8.5 minutes, 9 minutes, 9.5 minutes, 10 minutes, 11 minutes, 12 minutes, 13 minutes, 14 minutes to 15 minutes such as 0.5 minutes to 1.5 min on, followed by 0.5 minutes to 3.5 minutes off; 0.5 minutes to 2 minutes on, followed by 0.5 minutes to 3 minutes off; 0.5 minutes to 2 minutes on, followed by 0.5 minutes to 4 minutes off; 0.5 minutes to 2.5 minutes on, followed by 0.5 minutes to 2.5 minutes off; 0.5 minutes to 3 minutes on, followed by 0.5 minutes to 3 minutes off; 0.5 minutes to 3 minutes on, followed by 0.5 minutes to 4.5 minutes off; 0.5 minutes to 3 minutes on, followed by 0.5 minutes to 7 minutes off; 0.5 minutes to 4 minutes on, followed by 0.5 minutes to 6 minutes off; 0.5 minutes to 4 minutes on, followed by 0.5 minutes to 8 minutes off; 0.5 minutes to 5 minutes on, followed by 0.5 minutes to 5 minutes off; 0.5 minutes to 5 minutes on, followed by 0.5 minutes to 5 minutes off; 0.5 minutes to 5 minutes on, followed by 0.5 minutes to 5 minutes off; 0.5 minutes to 5 minutes on, followed by 0.5 minutes to 10 minutes off; 0.5 minutes to 6 minutes on, followed by 0.5 minutes to 14 minutes off; 0.5 minutes to 7 minutes on, followed by 0.5 minutes to 13 minutes off; 0.5 minutes to 8 minutes on, followed by 0.5 minutes to 12 minutes off, 0.5 minutes to 9 minutes on, followed by 0.5 minutes to 11 minutes off, or 0.5 minutes to 10 minutes on, followed by 0.5 minutes to 10 minutes off.

Multiple iontophoresis cycles can be used to apply current for a time period longer than 1 hour and less than 24 hours. Each cycle can be repeated one or more times, such as 2 to 300 times, 2 to 250 times, 2 to 200 times, 2 to 150 times, 2 to 100 times, 2 to 100 times, 2 to 50 times, 2 to 25 times, 2 to 20 times, 2 to 15 times, 2 to 10 times, or 2 to 5 times to have a total duration time of the applied current of 5 minutes to 30 minutes, 5 minutes to 1 hour, 1 hour to 5 hours, 1 hour to 10 hours, 1 hour to 15 hours, 1 hour to 20 hours, or 1 hour to 24 hours to improve drug transport and bioavailability. For example, the cycle can be 1.5 min on, followed by 3.5 min off, and repeated 12 times to have a total duration time of the applied current of 18 min, and a total time of application of iontophoresis from start to finish of 1 hour. Alternatively, the cycle can be 10 min on, followed by 10 min off, with this pattern repeated 3 times to have a total duration time of the applied current of 30 min, and a total time of application of iontophoresis from start to finish of 1 hour. Optionally, each cycle can use different parameters such as different current or time intervals. Optionally, there is a recovery time (rest period) between each cycle.

In some embodiments of any of the aspects, the iontophoresis is provided or performed in one or more cycles of iontophoresis, optionally wherein a cycle comprises delivering electrical current for a period of time ranging from 0.5 to 20 minutes followed by a recovery time period ranging from 0.5 to 20 minutes, e.g., a cycle comprises delivering electrical current for a period of time ranging from 0.5 to 15 minutes followed by a recovery time period ranging from 0.5 to 15 minutes, or e.g., a cycle comprises delivering electrical current for a period of time ranging from 0.5 to 10 minutes followed by a recovery time period ranging from 0.5 to 15 minutes.

In some embodiments of any of the aspects, iontophoresis, or the cycles of iontophoresis, is provided or performed for longer than one hour and less than 24 hours. In some embodiments of any of the aspects, iontophoresis, or the cycles of iontophoresis, is provided or performed for longer than 30 minutes and less than 24 hours. In some embodiments of any of the aspects, iontophoresis, or the cycles of iontophoresis, is provided or performed for longer than 30 minutes and less than 6 hours. In some embodiments of any of the aspects, iontophoresis, or the cycles of iontophoresis, is provided or performed for longer than 1 hour and less than 6 hours. In some embodiments of any of the aspects, iontophoresis, or the cycles of iontophoresis, is provided or performed for longer than 30 minutes and less than 3 hours. In some embodiments of any of the aspects, iontophoresis, or the cycles of iontophoresis, is provided or performed for longer than 1 hour and less than 3 hours.

Following oral delivery of the device, each of the electrodes adheres to different portions of the intestinal wall. The electrodes can extend away from the capsule to adhere to the intestinal wall. When the oral drug delivery device is in a carrier and/or the oral drug delivery device is in a capsule, the carrier or capsule will dissolve, disintegrate, and/or degrade following a suitable period of time or by an environmental change such as pH, temperature, or another environmental factor. When the oral drug delivery device is in a carrier, the carrier will first dissolve, disintegrate, and/or degrade before the electrodes can adhere to the intestinal wall.

Where the device is in the form of a dissolvable or degradable dosage form, such as a capsule, the device dissolves or degrades when the device is delivered to the intestine. The device also releases the drug reservoir containing the active agents, and the drug reservoir or the patch, film, or wafer in which the drug reservoir resides adheres to a wall of the intestine. Optionally, the device releases the agents directly to the intestinal mucosa.

Additionally, the drug reservoir attaches directly or indirectly to the same site or region of the intestinal wall as the electrodes. For example, when the drug reservoir is in physical contact with an electrode, the drug reservoir attaches at the same time and to the same site of the intestinal wall as the electrode. When the drug reservoir is in a separate compartment, patch or other oral delivery device than an electrode, then the drug reservoir attaches to a region of the mucosal surface that encompasses the site at which at least one electrode adheres, optionally the region encompasses both of the sites at which both electrodes adhere.

A biocompatible protective coating can cover the electrodes once they adhere to the intestinal wall and the application of iontophoresis is triggered.

Simultaneous with, or after, the application of iontophoresis to the intestine, the active agent is released from the drug reservoir to the intestinal mucosa, after applying the electric current for the iontophoresis. In some embodiments of any of the aspects, the active agent is not released from the device before iontophoresis begins. In some embodiments of any of the aspects, the active agent is released from the device after iontophoresis begins. In some embodiments of any of the aspects, the active agent is released from the device at least 10 minutes after iontophoresis begins. The release of the active agent from the drug delivery device can be triggered, e.g., by the change in the pH, by a timer, by a controller/trigger.

The drug delivery system can also be released from the intestinal mucosa following delivery or release of the active agents. The drug delivery device can be released from the intestinal mucosa by disintegration, enzymatic or hydrolytic degradation, loss of adhesion to the intestinal mucosa, or a combination thereof.

The drug delivery device can be in the body for a time period longer than 1 hour and less than 24 hours, between 1 hour to 24 hours, between 1 hour to 20 hours, between 1 hour and 15 hours, between 1 hour and 10 hours, between 1 hour and 5 hours, between 5 hours and 20 hours, between 5 hours and 15 hours, between 10 hours and 20 hours, between 10 hours and 24 hours, or between 12 hours and 24 hours. For example, the drug delivery device can be in the body between about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, and about 24 hours.

The devices and methods described herein can be administered to a subject including a human or an animal, such as a mammal including, but not limited to, a mouse, dog, cat, horse, bovine or ovine and the like, that is in need of treatment, alleviation or amelioration from a medical condition. For example, the devices described herein can be administered to a subject that suffers from type 1 or type 2 diabetes.

As used herein, "diabetes" refers to diabetes mellitus, a metabolic disease characterized by a deficiency or absence of insulin secretion by the pancreas. As used throughout, "diabetes" includes Type 1, Type 2, Type 3, and Type 4 diabetes mellitus unless otherwise specified herein. The onset of diabetes is typically due to a combination of hereditary and environmental causes, resulting in abnormally high blood sugar levels (hyperglycemia). The two most common forms of diabetes are due to either a diminished production of insulin (in type 1), or diminished response by the body to insulin (in type 2 and gestational). Both lead to hyperglycemia, which largely causes the acute signs of diabetes: excessive urine production, resulting compensatory thirst and increased fluid intake, blurred vision, unexplained weight loss, lethargy, and changes in energy metabolism. Diabetes can cause many complications. Acute complications (hypoglycemia, ketoacidosis, or nonketotic hyperosmolar coma) may occur if the disease is not adequately controlled. Serious long-term complications (i.e. chronic side effects) include cardiovascular disease (doubled risk), chronic renal failure, retinal damage (which can lead to blindness), nerve damage (of several kinds), and microvascular damage, which may cause impotence and poor wound healing. Poor healing of wounds, particularly of the feet, can lead to gangrene, and possibly to amputation. In some embodiments, the diabetes can be Type 2 diabetes. Type 2 diabetes (non-insulin-dependent diabetes mellitus (NIDDM), or adult-onset diabetes) is a metabolic disorder that is primarily characterized by insulin resistance (diminished response by the body to insulin), relative insulin deficiency, and hyperglycemia. In some embodiments, a subject can be pre-diabetic, which can be characterized, for example, as having elevated fasting blood sugar or elevated post-prandial blood sugar.

By "treatment" and "treating" is meant the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, amelioration, stabilization or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

The term "in need of treatment" refers to a judgment made by a caregiver (e.g. physician, nurse, nurse practitioner, or individual in the case of humans; veterinarian in the case of animals, including non-human mammals) that a subject requires or will benefit from treatment. This judgment is made based on a variety of factors that are in the realm of a care giver's expertise, but that include the knowledge that the subject is ill, or will be ill, as the result of a condition that is treatable by the compounds of the invention.

The numerical ranges provided herein are inclusive of all values in a given range. This includes the given minimum value, the given maximum value, as well as values between the minimum value and the maximum value, unless otherwise specified. For numerical ranges referring to integers, the ranges are inclusive of all integers between the minimum value and the maximum value, unless otherwise specified.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of diseases. A subject can be male or female.

A subject can be one who has been previously diagnosed with or identified as suffering from or having a condition in need of treatment (e.g. diabetes) or one or more complications related to such a condition, and optionally, have already undergone treatment for the condition or the one or more complications related to the condition. Alternatively, a subject can also be one who has not been previously diagnosed as having the condition or one or more complications related to the condition. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in in nature.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject. In some embodiments, administration comprises physical human activity, e.g., an injection, act of ingestion, an act of application, and/or manipulation of a delivery device or machine. Such activity can be performed, e.g., by a medical professional and/or the subject being treated.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean ±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method for oral drug delivery of an active agent to a subject in need thereof comprising:
   a) orally administering a drug delivery device to the subject, wherein the drug delivery device comprises the active agent; and
   b) triggering iontophoresis.

2. The method of paragraph 1, wherein the iontophoresis is triggered by an environmental stimulus, a timer, or a remote control.

3. The method of paragraph 1 or paragraph 2, wherein following step (a), the drug delivery device adheres to the intestinal mucosa.

4. The method of any one of paragraphs 1 to 3, further comprising (c) delivering the active agent to the intestinal mucosa, wherein step (c) occurs simultaneously with step (b).

5. The method of paragraph 4, further comprising, after step (c), releasing the drug delivery device from the intestinal mucosa.

6. The method of paragraph 5, the drug delivery device is released by disintegration, loss of adhesion to the intestinal mucosa, or a combination thereof.

7. The method of any one of paragraphs 1 to 6, wherein the iontophoresis is performed for a period of time and at an electrical current that is effective to improve permeability of a therapeutic agent across the intestine compared to orally administering the same drug delivery device in the absence of step (b).

8. The method of paragraph 7, wherein the electrical current for iontophoresis is in a range from 20 to 25 μA, from 25 to 30 μA, from 30 to 35 μA, from 35 to 40 μA, from 40 to 45 μA, from 45 to 50 μA, from 50 to 55 μA, or from 55 to 60 μA.

9. The method of paragraph 7, further comprising (d) performing one or more cycles of iontophoresis, optionally wherein a cycle comprises delivering electrical current for a period of time ranging from 0.5 to 10 minutes followed by a recovery time period ranging from 0.5 to 15 minutes.

10. The method of paragraph 9, wherein step (d) is performed for longer than one hour and less than 24 hours.

11. The method of any one of paragraphs 1 to 10, wherein the subject has type 1 or type 2 diabetes.

12. The method of any one of paragraphs 1 to 11, further comprising administering the active agent in an effective amount to treat one or more symptoms in the subject in need of treatment.

13. The method of paragraph 12, wherein the active agent is administered in an effective amount to reduce blood glucose levels.

14. The method of any one of paragraphs 1 to 13, further comprising administering the oral drug delivery device to improve transport and bioavailability of the active agent.

15. The method of any one of paragraphs 1 to 14, further comprising attaching at least two electrodes to a wall of the intestine, following step (a).

16. The method of paragraph 15, further comprising releasing a biocompatible protective coating from the drug delivery device to cover the electrodes prior to step (b).

17. The method of paragraph 15, wherein each of the electrodes extends in opposite directions from the capsule.

18. An intestinal iontophoretic device comprising a mucoadhesive patch and two electrodes, wherein the mucoadhesive patch comprises an active agent to be delivered.

19. The device of paragraph 18, wherein the active agent is a small molecule or a macromolecule.

20. The device of paragraph 18 or paragraph 19, wherein the macromolecule is a protein or peptide.

21. The device of any one of paragraphs 18 to 20, wherein the active agent is insulin or an analog thereof.

22. The device of any one of paragraph 18 to 20, further comprising a power supply.

23. The device of paragraph 22, wherein the power supply is a chip battery.

24. The device of paragraph 22 or paragraph 23, further comprising an electrical circuit that connects the power supply to the electrodes.

25. The device of any one of paragraph 18 to 24, further comprising a drug release trigger.

26. The device of paragraph 25, wherein the drug release trigger is a timer, a pH or temperature sensor, or a combination thereof.

27. The device of any one of paragraphs 22 to 26, wherein the power supply is attached to the electrodes through a flexible, coated electrically conductive material.

28. The device of any one of paragraphs 18 to 27, wherein the patch comprises one or more compartments, wherein at least one compartment is a reservoir comprising the active agent.

29. The device of paragraph 28, wherein at least one compartment is a mucoadhesive compartment.

30. The device of any one of paragraphs 18 to 29, further comprising a capsule, wherein the mucoadhesive patch is inside the capsule.

31. The device of any one of paragraphs 18 to 30, wherein the device further comprises a microsensor, microactuator, microelectronics, or a combination thereof.

32. The device of any one of paragraphs 18 to 31, wherein the electrodes are at least 0.5 cm, 1 cm, 2 cm, 3 cm, 4 cm, or 5 cm apart from each other.

33. The device of any one of paragraphs 30 to 32, wherein the capsule further comprises one or more compartments, wherein at least one compartment comprises the patch.

34. The device of paragraph 33, wherein at least one compartment comprises the power supply.

35. The device of any one of paragraphs 30 to 34, wherein the capsule is enterically coated.

36. The method of any one of paragraphs 1 to 17, wherein the oral drug delivery device is the intestinal iontophoretic device of any one of paragraphs 18-35.

37. A system for oral drug delivery of an active agent to a subject in need thereof comprising:
    a) a control unit; and
    b) the intestinal iontophoretic device of any one of paragraphs 18-35.

38. The system of paragraph 37, wherein the control unit is external.

39. The system of paragraph 37, wherein the external control unit is internal.

40. The system of paragraph 37, wherein the control unit is in electrical communication with the oral drug delivery device.

41. The system of paragraph 38, wherein the external control unit is a remote control.

42. The system of paragraph 41, wherein the remote control is configured to switch control the drug delivery device, such as by switching it on and off.

43. The system of paragraph 41, wherein the remote control is configured to trigger iontophoresis, release of the active agent, release of the drug delivery device from the intestinal mucosa, or a combination thereof.

44. The system of paragraph 43, wherein the remote control is configured to modify iontophoresis parameters.

45. The system of paragraph 43, wherein the external control unit comprises a power supply.

46. The system of paragraph 45, wherein the power supply comprises an external battery.

Some embodiments of the technology described herein can be defined according to any of the following numbered paragraphs:

1. A method for oral drug delivery of an active agent to a subject in need thereof comprising:
   a) orally administering an iontophoretic drug delivery device to the subject, wherein the iontophoretic drug delivery device comprises the active agent.

2. A method for oral drug delivery of an active agent to a subject in need thereof comprising:
   a) orally administering a drug delivery device to the subject, wherein the drug delivery device comprises the active agent; and
   b) triggering iontophoresis.

3. The method of paragraph 2, wherein the iontophoresis is triggered by an environmental stimulus, a timer, or a remote control.

4. The method of any of paragraphs 1 to 3, wherein following step (a), the drug delivery device adheres to the intestinal mucosa.

5. The method of any one of paragraphs 2 to 4, further comprising (c) delivering the active agent to the intestinal mucosa, wherein step (c) occurs simultaneously with step (b).

6. The method of paragraph 5, further comprising, after step (c), releasing the drug delivery device from the intestinal mucosa.

7. The method of paragraph 6, wherein the drug delivery device is released by disintegration, loss of adhesion to the intestinal mucosa, or a combination thereof.

8. The method of any one of paragraphs 1 to 7, wherein iontophoresis is performed for a period of time and at an electrical current that is effective to improve permeability of a therapeutic agent across the intestine compared to orally administering the same drug delivery device in the absence of iontophoresis.

9. The method of paragraph 8, wherein the electrical current for iontophoresis is in a range from 20 to 25 µA, from 20 to 30 µA, from 25 to 30 µA, from 30 to 35 µA, from 35 to 40 µA, from 40 to 45 µA, from 40 to 55 µA, from 45 to 55 µA, from 45 to 50 µA, from 50 to 55 µA, or from 55 to 60 µA.

10. The method of any of paragraphs 8 to 9, wherein the iontophoresis is provided or performed in one or more cycles of iontophoresis, optionally wherein a cycle comprises delivering electrical current for a period of time ranging from 0.5 to 20 minutes followed by a recovery time period ranging from 0.5 to 20 minutes.

11. The method of any of paragraphs 8 to 9, wherein the iontophoresis is provided or performed in one or more cycles of iontophoresis, optionally wherein a cycle comprises delivering electrical current for a period of time ranging from 0.5 to 15 minutes followed by a recovery time period ranging from 0.5 to 15 minutes.

12. The method of any of paragraphs 8 to 9, wherein the iontophoresis is provided or performed in one or more cycles of iontophoresis, optionally wherein a cycle comprises delivering electrical current for a period of time ranging from 0.5 to 10 minutes followed by a recovery time period ranging from 0.5 to 15 minutes.

13. The method of any of paragraphs 8 to 12, wherein iontophoresis, or the cycles of iontophoresis, is provided or performed for longer than one hour and less than 24 hours.

14. The method of any of paragraphs 8 to 12, wherein iontophoresis, or the cycles of iontophoresis, is provided or performed for longer than 30 minutes and less than 24 hours.

15. The method of any of paragraphs 1 to 14, wherein the active agent is not released from the device before iontophoresis begins.

16. The method of any of paragraphs 1 to 14, wherein the active agent is released from the device after iontophoresis begins.

17. The method of any of paragraphs 1 to 14, wherein the active agent is released from the device at least 10 minutes after iontophoresis begins.

18. The method of any one of paragraphs 1 to 17, further comprising attaching at least two electrodes to a wall of the intestine, following step (a).

19. The method of paragraph 18, further comprising releasing a biocompatible protective coating from the drug delivery device to uncover the electrodes prior to step (b).

20. The method of any one of paragraphs 1 to 17, wherein the device comprises a biocompatible protective coating which covers at least two electrodes.

21. The method of any of paragraphs 19 to 20, wherein the biocompatible protective coating is an enteric coating that dissolves or degrades before or upon reaching the intestine.

22. The method of any of paragraphs 18 to 21, wherein the at least two electrodes extends in opposite directions from the capsule.

23. The method of any one of paragraphs 1 to 22, whereby administering the oral drug delivery device improves transport and bioavailability of the active agent.

24. The method of any of paragraphs 1 to 23, wherein the active agent is a small molecule or macromolecule.

25. The method of any one of paragraphs 1 to 24, wherein the active agent is administered or present in the device in an effective amount to treat one or more symptoms in the subject in need of treatment.

26. The method of any one of paragraphs 1 to 25, wherein the subject has type 1 or type 2 diabetes.

27. The method of paragraph 26, wherein the active agent is administered in an effective amount to reduce blood glucose levels.

28. The method of paragraph 27, wherein the active agent is insulin or an analog thereof.

29. The method of any of paragraphs 1 to 28, wherein the active agent is administered or present in the device at a dosage of from 1 U/kg to 100 U/kg.

30. The method of any of paragraphs 1 to 29, wherein the active agent is administered or present in the device at a dosage of from 40 U/kg to 60 U/kg.

31. The method of any of paragraphs 1 to 28, wherein the active agent is administered or present in the device at a dosage of 50 U/kg.

32. The method of any of paragraphs 1 to 31, wherein the device is a device according to any of the following paragraphs.

33. An intestinal iontophoretic device comprising at least two electrodes and an active agent.

34. The device of paragraph 33, wherein the device comprises an outer biocompatible protective coating that encapsulates the electrodes and active agent.

35. The device of paragraph 34, wherein the biocompatible protective coating is an enteric coating.

36. The device of any of paragraphs 33 to 35, further comprising a mucoadhesive patch.

37. The device of paragraph 36, wherein the mucoadhesive patch comprises the active agent.

38. The device of any of paragraphs 33 to 37, wherein the active agent is a small molecule or a macromolecule.

39. The device of paragraph 38, wherein the macromolecule is a protein or peptide.

40. The device of any one of paragraphs 38 to 39, wherein the active agent is insulin or an analog thereof.

41. The device of any one of paragraphs 33 to 37, further comprising a power supply.

42. The device of paragraph 41, wherein the power supply is a chip battery.

43. The device of paragraph 41 or 42, further comprising an electrical circuit that connects the power supply to the electrodes.

44. The device of any one of paragraphs 41 to 43, wherein the power supply is attached to the electrodes through a flexible, coated electrically conductive material.

45. The device of any one of paragraphs 33 to 44, further comprising a drug release trigger.

46. The device of paragraph 45, wherein the drug release trigger is a timer, a pH or temperature sensor, a wireless receiving module, or a combination thereof.

47. The device of any one of paragraphs 33 to 46, wherein the patch comprises one or more compartments, wherein at least one compartment is a reservoir comprising the active agent.

48. The device of paragraph 47, wherein at least one compartment is a mucoadhesive compartment.

49. The device of any one of paragraphs 33 to 48, further comprising a capsule, wherein the mucoadhesive patch is inside the capsule.

50. The device of any one of paragraphs 33 to 49, wherein the device further comprises a microsensor, microactuator, microelectronics, or a combination thereof.

51. The device of any one of paragraphs 33 to 50, wherein the electrodes are at least 0.5 cm, 1 cm, 2 cm, 3 cm, 4 cm, or 5 cm apart from each other.

52. The device of any one of paragraphs 33 to 51, wherein the capsule further comprises one or more compartments, wherein at least one compartment comprises the patch.
53. The device of paragraph 52, wherein at least one compartment comprises the power supply.
54. The device of any one of paragraphs 49 to 53, wherein the capsule is enterically coated.
55. The device of any of paragraph 33 to 54, further comprising a transmitter which can transmit on or more of: location information, time of the start of drug release, elapsed time of drug release, drug release duration, remaining drug dosage, and iontophoresis activity.
56. A system for oral drug delivery of an active agent to a subject in need thereof comprising:
   a) a control unit; and
   b) the intestinal iontophoretic device of any one of paragraphs 33 to 55.
57. The system of paragraph 56, wherein the control unit is external.
58. The system of paragraph 56, wherein the external control unit is internal.
59. The system of any of paragraphs 56 to 58, wherein the control unit is in electrical communication with the oral drug delivery device.
60. The system of paragraph 59, wherein the external control unit is a remote control.
61. The system of paragraph 60, wherein the remote control is configured to switch control the drug delivery device, such as by switching it on and off.
62. The system of any of paragraphs 60 to 61, wherein the remote control is configured to trigger iontophoresis, release of the active agent, release of the drug delivery device from the intestinal mucosa, or a combination thereof.
63. The system of any of paragraphs 60 to 62, wherein the remote control is configured to modify iontophoresis parameters.
64. The system of any of paragraphs 57 to 63, wherein the external control unit comprises a power supply.
65. The system of paragraph 64, wherein the power supply comprises an external battery.

EXAMPLES

Example 1

In Vitro FITC-Insulin Transport Across Caco-2 Monolayers Assay

Materials and Methods

Materials

Human Insulin, fluorescein isothiocyanate (FITC)-insulin, pectin, sodium carboxy methylcellulose (SCMC), hematoxylin and eosin solutions were bought from Sigma-Aldrich (St. Louis, MO, USA). Eudragit® EPO was received as a gift from Evonik Industries (Parsipanny, NJ, USA). Caco-2 human colorectal adenocarcinoma cells were purchased from American Type Culture Collection (Manassas, VA, USA). All cell culture solutions including Dulbecco modified eagle medium (DMEM) with or without phenol red, fetal bovine serum (FBS), penicillin/streptomycin (P/S) solution, Hank's balanced salt solution (HBSS) and 0.25% trypsin solution were obtained from Thermo Fisher Scientific (Waltham, MA, USA). The transwells Millicell®-PCF cell culture inserts (3.0 μm pore size, 12 mm diameter) and trans epithelial electrical resistance (TEER) measuring device, Millicell®-ERS were bought from Millipore Sigma (Burlington, MA, USA). Electrodes for measuring TEER were purchased from World Precision Instruments, Inc (Sarasota, FL, USA). Paraformaldehyde (16% w/v) was obtained from Alfa Aesar (Ward Hill, MA, USA) while Vectashield Hardset™ with 4',6-diamidino-2-phenylindole, dihydrochloride (DAPI) was bought from Vector laboratories Inc. (Burlingame, CA, USA). The patches were prepared using a bench top press (Carver, Inc., Wabash, IN, USA) and a pellet press (Pike Technologies, Fitchburg, WI, USA). Royovac heavy-duty 6 V lantern battery with screw tops was obtained from Fisher Scientific (Waltham, MA, USA) while analog panel current ammeters (0-200 μA DC) and 100K-ohm audio-taper potentiometers were bought from local stores. Male Wistar rats (200-300 g) were purchased from Charles River Laboratories (Wilmington, MA, USA) while blood glucose measuring meter (Aimstrip plus) and strips were purchased from Fisher Scientific (Pittsburgh, PA, USA). All other reagents were of analytical grade.

Caco-2 Monolayer Culture in Transwells

Caco-2 human intestinal epithelial cells (passages #5-10) were cultured in DMEM containing 10% v/v FBS and 1% v/v P/S and seeded in 24 well plate transwells at a density of $2\times10^5$ cells/ml. 200 μl DMEM with cells was placed in apical side while 600 μl cell free DMEM was placed in the basolateral side. The cells were allowed to grow for a period of 18-21 days and medium replaced with fresh DMEM every other day. TEER was measured on a regular basis and when it reached above 200 ohms·cm$^2$, indicating sufficient tight junction integrity between the cells in the monolayer, iontophoretic transport study of insulin was performed.

Circuit Setup and FITC-Insulin Transport Assay

The circuit for in vitro transport study was set up as shown in FIG. 1. To maintain sterile conditions, all in vitro experiments including circuit set up were done under aseptic conditions in a biosafety cabinet. A 6 V battery was used to supply electrical current to transwells containing Caco-2 monolayer. The higher potential of the battery was connected to the basolateral side of the transwell while the lower potential of the battery connected to the apical side while taking care not to touch the transwell membranes with Caco-2 cell monolayer. The current applied to the cell was monitored by an ammeter and its value was adjusted to 50 μA using a potentiometer. Three different branches, each attached to an ammeter, potentiometer and transwell were connected in parallel across the battery to enable three different measurements at a time.

Transport experiments were carried out in triplicates and at least 3 transwells were used per trial for each group. Before the start of the experiment, the existing medium in the transwell was replaced with phenol red, FBS and P/S free DMEM in both the apical (200 μl) and basolateral side (600 μl) and the cells were incubated for 30 minutes. At the start of study, the medium in the apical side was replaced with 200 μl of 500 μg/ml FITC-insulin prepared in phenol red, FBS and P/S free DMEM. Immediately after addition of FITC-insulin at the apical side, a 100 μl aliquot was withdrawn from the basolateral side and replaced with same volume fresh DMEM. This was performed at 0.25, 0.5, 1, 2, 3 and 5 h. A 50 μA electrical current was applied to the cells during the first hour of the study for a period of 10 min, followed by 10 min recovery period and this was repeated another two times. At the end of 1 h (total 30 minutes iontophoresis), the transwell plates were kept inside an incubator at 37° C., 5% CO$_2$ and only taken out to remove 100 μl aliquots from the basolateral side followed by replacement with same volume fresh medium at the aforementioned time periods. After the end of study at 5 h, the FITC-insulin concentration in the aliquots were measured at 495/520 nm excitation/emission wavelengths using a Tecan Infinite M200 Pro multimode reader (Tecan US, Inc, Morrrisville, NC, USA microplate reader). Results were plotted as % FITC-insulin transport vs time. TEER was measured at every time point when aliquots were withdrawn from the transwells. Apparent permeability coefficient (Papp) was calculated using the equation (Brown, et al., "Dermal and transdermal drug delivery systems: current and future prospects," *Drug Deliv.* 13(3):175-87 (2006)):

$$Papp = \frac{dQ}{dt} \times \frac{1}{A \cdot C0}$$

where dQ/dt is calculated from the slope of cumulative insulin transport across Caco-2 cells with respect to time, A is the area of the transwell surface and C0 is the insulin concentration in the apical side at time 0. The transport enhancement ratio (ER) was calculated using the equation (Brown, et al., 2006):

$$ER = \frac{Papp \text{ iontophoresis}}{Papp \text{ control}}$$

Confocal Microscopy

For qualitative analysis of FITC-insulin uptake by Caco-2 cells, the transwells from FITC-insulin transport study were washed two times with HBSS, followed by addition of 100 μl of 4% paraformaldehyde and kept at 4° C. overnight. On the next day, the transwells were washed with HBSS and the membrane cut out and placed in glass slides. Mounting media with DAPI was added to the membranes and covered with glass slides. Confocal imaging was performed using Olympus Fluoview 1000 Spectral Confocal instrument at 60× magnification.

Results

FITC-Insulin Transport

Figure 4:
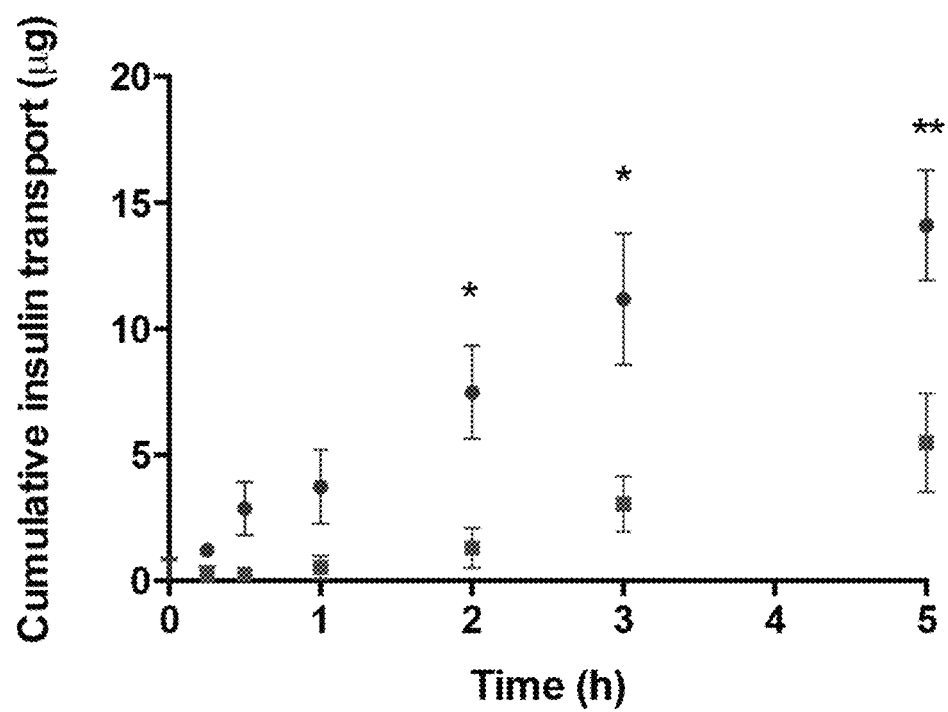
FIG. 4 is a line graph of FITC-insulin transport across Caco-2 monolayers with (circles) and without (squares) the application of electric current versus time (hours). Data are represented as mean±SD. A significantly higher insulin transport across the cells was observed from 2 hours onwards upon application of electric current (circles) compared to control cells that were not subjected to treatment with electric current (squares) (* $p<0.05$, ** $p<0.01$), n=3.

The transport of FITC-insulin across Caco-2 monolayers upon application of electrical current was first assessed. Transport was higher with electrical current right from the onset of study at 15 min (1.2 μg in electric current group compared to 0.2 μg in control group) but it improved significantly (p<0.01-0.05) from 2 h onwards (FIG. 4). At the end of 5 h, approximately 14.1 μg FITC-insulin was transported across the cells to which electric current was applied compared to only about 5.5 μg transport in control group. The Papp of FITC-insulin across the cells in 5 h was $26.4 \times 10^{-7}$ cm/sec with electricity while that without electricity was $9.9 \times 10^{-7}$ cm/sec. The Papp value of insulin in control cells was very comparable to those obtained by other researchers using 21-day Caco-2 monolayer cultures (Philip, et. al., "Iontophoretic delivery of peptide drugs," *J Controlled Release*, 8; 41(1-2):33-48 (1996.); Alkilani, et al., "Transdermal Drug Delivery: Innovative Pharmaceutical Developments Based on Disruption of the Barrier Properties of the stratum corneum," *Pharmaceutics*, 7(4):438-70 (2015); Martanto, et al., "Transdermal delivery of insulin using microneedles in vivo," *Pharm Res*, 21(6):947-52 (2004). The enhancement ratio calculated from the Papp was 2.7.

The higher transport of insulin across Caco-2 cells was corroborated by confocal images of transwell membranes that showed presence of higher FITC-insulin in cells subjected to iontophoresis.

Figure 5:
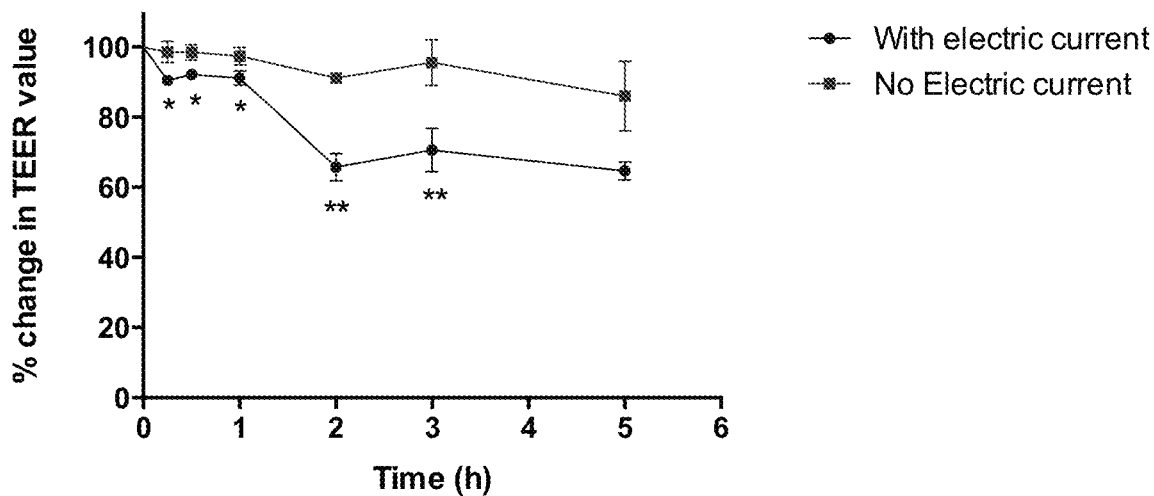
FIG. 5 is a line graph of % change in TEER value for Caco-2 cells with (circles) and without (squares) the application of electric current versus time (hours). Data are represented as mean±SD. A significant reduction in TEER in cells was observed upon application of electric current for 15 minutes (circles) compared to no electric current applied to control cells (squares) (* $p<0.05$, ** $p<0.01$), n=3.

Measurement of Tight Junction Integrity in Caco-2 Monolayers Upon Application of Electric Current TEER was measured to determine the tight junction integrity in Caco-2 cells upon application of electric current. TEER decreased significantly (p<0.05) by 10% within 15 min of passage of current compared to no specific decrease in the control group (FIG. 5). After 2 h of the study, TEER dropped more significantly by 35% of initial levels (65.7±3.8%) and was relatively constant during the remaining 3 hours of the study. In comparison, in control (no current) wells, TEER reduced by around 9% and 4% of initial levels in 2 and 3 hours respectively (91.2±1.1% and 95.6±6.5%).

As shown, transport of insulin across intestinal cells was 2.7-fold higher with the application of intermittent electric current during first hour of the study compared to no current control. This can be attributed to significant decline in TEER from the onset of the experiment with a maximal 35% drop at 2 h. Insulin transport across the cells was also significantly higher than control from 2 hours onwards when TEER drop was maximum. The reduction in TEER suggests that insulin transport across Caco-2 monolayer subjected to electric current is mostly paracellular. At the end at 5 hours, no significant difference in TEER between control and electric current group was observed, indicating that tight junction integrity may recover with time.

Confocal Micrograph Images

Confocal laser scanning microscopy images of transwell membranes of wells with or without iontophoresis showed higher uptake of FITC-insulin by cells exposed to electric current compared to control wells.

Example 2

In Vivo Intestinal Iontophoresis Using Mucoadhesive Patches

Materials and Methods

Insulin Mucoadhesive Patch Preparation

Figure 2:
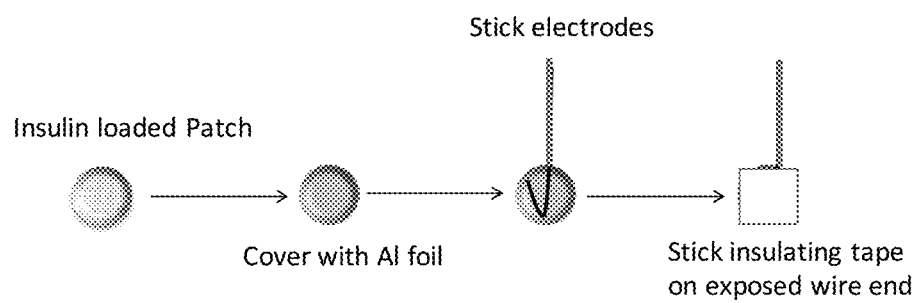
FIG. 2 is a schematic illustrating the steps used to prepare the iontophoretic mucoadhesive patches used in Example 2.

Insulin mucoadhesive patches were prepared as described in Banerjee, et al., "Intestinal Mucoadhesive Devices for Oral Delivery of Insulin," *Bioeng. Transl. Med.* 1, 338-346 (2016). Briefly, Eudragit E PO, pectin and SCMC were mixed in the ratio of 1:1:2 and known quantity of insulin was added to the mixture. About 110 mg of the mixture was pressed at 3-ton pressure using a hydraulic press into a patch. The patches were then cut into 5×3 mm (length× breadth) sized rectangular smaller patches. For intestinal iontophoresis, the patches were further processed as shown in FIG. 2. One side of the patch was completely covered with aluminum foil using minimal amount of super glue placed at one corner of the foil. Wires with a small section of their protective insulation removed were then stuck on the aluminum foil using super glue. Care was taken not to cover the entire wire placed over the foil with super glue. The exposed wire sticking on to the patches were then taped with an electrical insulating tape to prevent any loss of current in vivo through exposed wire. The insulin doses used in the patches were either 25 or 50 U/kg.

Figure 3:
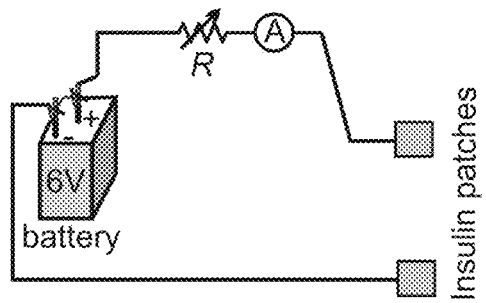
FIG. 3 is a schematic of an exemplary in vivo iontophoresis circuit, which was used in Example 2.

Circuit Setup and In Vivo Efficacy Study of Intestinal Iontophoresis Using Insulin Mucoadhesive Patches All animal experiments were performed in accordance with the University of California Santa Barbara animal care committee guidelines and to the Guide for the Care and Use of Animals of the Institute of Laboratory Animal Resources, National Research Council. The circuit for in vivo experiments was set up as illustrated in FIG. 3.

Intestinal iontophoresis was carried out using a 6 V battery connected to the intestine. A potentiometer and an ammeter were used in the electrical circuit to accurately control and measure the electric current. Given that the identified safe threshold for iontophoresis is 0.5 mA/cm$^2$, the electrical parameters were selected in order to perform the studies using a safe current density of 0.33 mA/cm$^2$ (Singh, et. al., "Transdermal drug delivery by passive diffusion and iontophoresis: a review," Med Res Rev., 13(5): 569-621 (1993)). For the experiment, the rats were fasted overnight but given free access to water. Prior to the start of intestinal iontophoresis, the rats were anesthetized, a portion of abdomen prepped for surgery and an incision was made in the area to expose the intestine. Experiments were conducted using sterile instruments and following good surgical practices. Two small cuts about 5 cm afar were made in a small exposed section of the intestine and patches containing 50 U/kg insulin connected to wires and battery source were inserted. Thereafter current (45-50 μA) was allowed to flow for 1.5 minutes followed by 3.5 minutes of recovery time for 1 h, amounting to a total 18 min of iontophoresis. After 1 h, the patches were left in place but the wires were disconnected from the battery and cut close to the inserted patches. The intestinal incisions with the patches left in place were stitched, the intestine put back into the abdomen and the muscle and skin sutured. Blood glucose was determined at the start of the study and at every 0.5 h till the end of study at 3 h. The rats were kept anesthetized until the end of experiment. Afterwards, the animals were euthanized and the intestinal sections in and around the patches were dissected for further histological examination to determine morphological changes, if any, due to iontophoresis.

Control experiments with no electric current were conducted similarly. Additionally, subcutaneous (SQ) administration of 1 U/kg insulin solution was performed in 3 rats for comparison of efficacy. To determine whether decrease in current or insulin dose would bring about similar efficacy, studies were conducted using 50 μA current with patches containing 25 U/kg insulin or using 25 μA current with 50 U/kg insulin patches.

Tissue Histology

Tissues were fixed in 10% buffered formalin, dehydrated in ethanol, and embedded in paraffin. Five-micron cross-sections of intestine tissues were deparaffinzed, rehydrated, and stained with hematoxylin and eosin. Histological morphology was examined using a light microscope (Olympus BX60 Upright Compound Microscope).

Statistical Analysis

All in vitro data are presented as mean±standard deviation (SD) while in vivo data are presented as mean±standard error (SE). The statistical analyses were performed using two-tailed student's t-test and p value less than 0.05 was considered statistically significant. Graphs were plotted using Graphpad Prism 6.0™, (GraphPad Software, La Jolla, CA).

Results

In Vivo Intestinal Iontophoresis Using Mucoadhesive Patches

Figure 6:
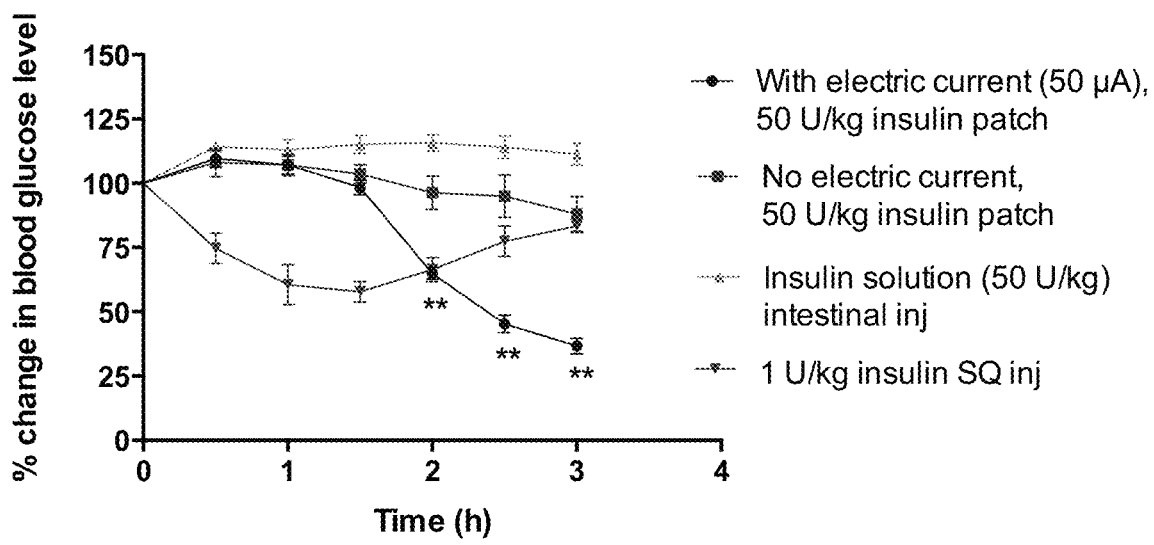
FIG. 6 is a line graph of % change in blood glucose level in non-diabetic rats versus time (hours). Data for electric current (50 µA) applied with a 50 U/kg insulin patch (circles), no electric current applied with 50 U/kg insulin patch (squares); insulin solution (50 U/kg) intestinal injection (upward triangles ▲); insulin solution subcutaneous injection (downward triangles ▼) are shown. A significantly higher reduction in blood glucose levels was observed using insulin patch based intestinal iontophoresis from 2 hours onwards (circles) compared to control insulin patch (no electric current, squares). Data are represented as mean±SE. (** $p<0.01$, electric current group compared to no electric current group), n=6 for iontophoresis and controls and n=3 for SQ injection.

Iontophoresis was performed at an intestinal site and good correlation with in vitro data was observed. Rats with 50 U/kg insulin patches inserted in their intestine and subjected to 45-50 μA current, demonstrated a significant (p<0.01) drop in blood glucose levels from 2 hours onwards to 35% of initial levels (65±2.2%) that further decreased to 63% (36.6±3%) in 3 hours (FIG. 6). In contrast, rats with 50 U/kg insulin patches but without electric current treatment, showed only 3.4% drop in 2 hours (96.4±6.6%) followed by a maximum 12% drop in 3 hours (88.1±6.7%). Rats that were intra-intestinally injected with 50 U/kg insulin solution did not show any drop in blood glucose levels with time while those subcutaneously injected with 1 U/kg insulin solution showed a maximum drop of 42% in 1.5 h (57.9±4.1%) that recovered to about 17% of initial levels (83.3±2.6%) in 3 h.

Figure 7:
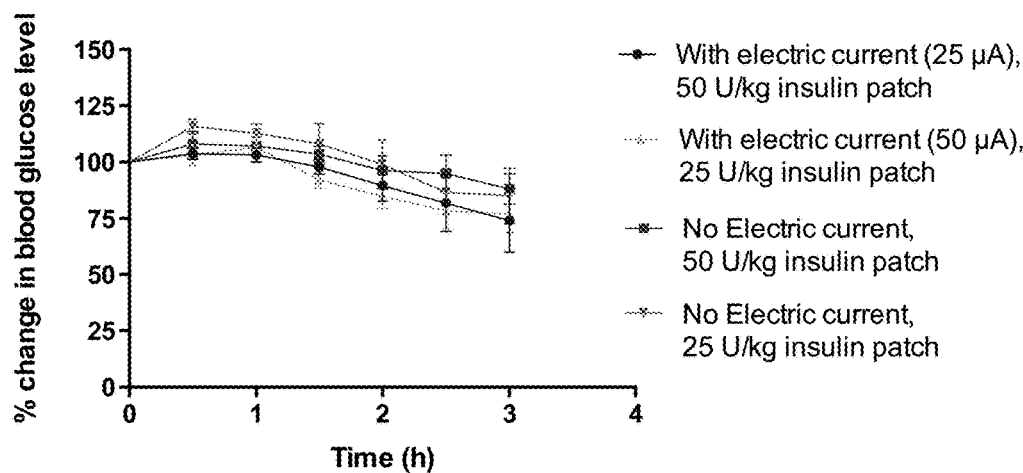
FIG. 7 is a line graph of % change in blood glucose level in non-diabetic rats versus time (hours). Data for low electric current (25 µA) applied with a 50 U/kg insulin patch (circles), high electric current (50 µA) applied with a low insulin concentration 25 U/kg insulin patch (upward triangles ▲), no electric current applied with 50 U/kg insulin patch (squares); no electric current applied with a low insulin concentration 25 U/kg insulin patch (downward triangles ▼) are shown. No significant difference in blood glucose lowering efficacy of the patches was observed between the iontophoresis group (circles and upward triangles) and the respective controls (no current applied) (squares and downward triangles). Data represented as mean±SE. (n=6).

Effect of Varying Electrical Current and Insulin Dose on Blood Glucose Reduction The experiments were repeated using a lower current or a lower insulin dose. A lower current of 20-25 μA was applied for the same duration as described above. Additionally, the insulin dose was the same (18 minutes and 50 U/kg respectively). Lowering the current value to 20-25 μA did not bring about a significant drop in blood glucose and a maximum 26% (74.04±14.2% of initial level) decrease was noted in 3 h (FIG. 7). In comparison, same dose-no electric current control rats demonstrated only 12% (88.1±6.7% of initial level) drop in blood glucose in 3 h.

Next, blood glucose lowering efficacy by reducing insulin dose to 25 U/kg but keeping current and treatment duration same (45-50 μA current and 18 min respectively) was investigated. This modification also did not bring about a significant drop in blood glucose levels and a maximum decrease of 23% (77.1±8.8% of initial level) in 3 h was observed while its respective no electric current control resulted in a 15% drop (85±12.2% of initial level).

Assessment of Toxicity to Intestinal Tissue Upon Application of Electric Current Histological examination showed no difference with regard to morphology of intestinal tissue between the groups of rats with or without iontophoretic treatment. In particular, sections where patches were placed or adjacent areas showed no structural damage upon the application of electric current. The lumen of the intestine (lamina propria and intestinal gland) was intact, and the thickness of smooth muscles was similar among all the tissues when measured with light microscopy.

Iontophoresis Further Enhanced the Efficacy of Intestinal Mucoadhesive Patches in Oral Insulin Delivery.

Iontophoresis greatly enhanced transport of insulin across the intestine leading to a significant 63% drop in blood glucose levels. Also, a significant drop in blood glucose levels was observed at 2 hours of the study that steadily declined until 3 hours when animals became severely hypoglycemic and the study was terminated. However, modulation of electric current or insulin doses did not produce such significant efficacy.

Example 3

Biologics have limited permeability across the intestine and are prone to degradation in the acidic-proteolytic milieu of the gastrointestinal tract, leading to poor oral bioavailability. Iontophoresis is a promising technology that can substantially improve transport of drugs across biological barriers and has been particularly explored for skin. In this study, we investigated whether iontophoresis across the intestine can be utilized to improve oral insulin transport. Application of electric current to intestinal cells resulted in opening of the tight junctions in vitro and a consequent about 3-fold improvement in paracellular transport of insulin. When evaluated in vivo using insulin-loaded mucoadhesive patches, iontophoresis produced profound hypoglycemia (63% blood glucose drop in 3 h) without damaging the intestinal tissue and the efficacy depended on insulin dose and current density. This study presents a proof of principle for intestinal iontophoresis as a novel method for oral protein delivery.

Oral delivery is the favored route for drug administration by both patients and physicians due to its ease of administration. However, its use for biologics is limited because of their susceptibility to gastrointestinal degradation and limited permeability across the epithelium, leading to negligible oral bioavailability. This necessitates parenteral delivery of these therapeutic macromolecules, which lacks patient compliance and often results in non-adherence to dosing regimen, especially in the long-term. Various alternative approaches for oral delivery of biologics have been investigated including modification in protein/peptide structure to impart resistance to degradation by gastrointestinal acids and enzymes and/or improve permeability across intestinal wall, encapsulating them in enterically coated carriers or other novel formulations, using permeation enhancers and proteolytic inhibitors, amongst others [1-3]. We have earlier developed mucoadhesive intestinal patches for oral delivery of biologics such as insulin and salmon calcitonin and observed considerable improvement in oral bioavailability of the drugs [4,5]. These patches made using a specific combination of mucoadhesive polymers and coated with a water impermeable backing layer, improved intestinal permeability by strongly adhering to intestinal mucosa and providing a unidirectional transport of biologics from the drug depot in the patches. Additionally, the patches prevented enzymatic degradation of biologics by preventing access of intestinal enzymes to the loaded drugs. Furthermore, encapsulation of the patches in enterically coated capsules led to site specific delivery to the intestine. To further improve efficacy of the patches, in the current study we explored intestinal iontophoresis as a novel method to facilitate permeation of insulin across intestine both in vitro and in vivo.

Iontophoresis is a procedure that has been extensively used to enhance transport of drugs across biological barriers such as the skin [6-9]. The technique utilizes an electric current gradient to drive ionic or non-ionic drugs across the barriers and has been primarily utilized for treatment of hyperhidrosis, local inflammation and pain. The skin restricts passive transport of hydrophilic drugs or those with molecular weight>500 Da but with iontophoresis, controlled and painless delivery of many such medications is possible. Using small current gradient for short periods of time (generally ≤0.5 mA/cm2 and 30 min for transdermal delivery), tissue trauma and risk of infections can be minimized using iontophoresis, unlike injectables [8]. In addition, a precise dose of medication can be delivered directly to the treatment site or systemically and the treatment can be terminated when desired by simply switching off the iontophoretic system [8,10]. Iontophoresis has not previously been utilized in the context of oral drug delivery. Here, we investigate if iontophoresis can be utilized to improve permeation of insulin across the intestinal cells, thus improve oral delivery of insulin.

Materials and Methods

Materials

Human Insulin, fluorescein isothiocyanate (FITC)-insulin, pectin, sodium carboxy methylcellulose (SCMC), hematoxylin and eosin solutions were bought from Sigma-Aldrich (St. Louis, MO, USA). Eudragit® E PO was received as a gift from Evonik Industries (Parsipanny, NJ, USA). Caco-2 human colorectal adenocarcinoma cells were purchased from American Type Culture Collection (Manassas, VA, USA). All cell culture solutions including Dulbecco modified eagle medium (DMEM) with or without phenol red, fetal bovine serum (FBS), penicillin/streptomycin (P/S) solution, Hank's balanced salt solution (HBSS) and 0.25% trypsin solution were obtained from Thermo Fisher Scientific (Waltham, MA, USA). The transwells Millicell®-PCF cell culture inserts (3.0 μm pore size, 12 mm diameter) and trans epithelial electrical resistance (TEER) measuring device, Millicell®-ERS were bought from Millipore Sigma (Burlington, MA, USA). Electrodes for measuring TEER were purchased from World Precision Instruments, Inc. (Sarasota, FL, USA). Paraformaldehyde (16% w/v) was obtained from Alfa Aesar (Ward Hill, MA, USA) while Vectashield Hardset™ with 4',6-diamidino2-phenylindole, dihydrochloride (DAPI) was bought from Vector laboratories Inc. (Burlingame, CA, USA). The patches were prepared using a bench top press (Carver, Inc., Wabash, IN, USA) and a pellet press (Pike Technologies, Fitchburg, WI, USA). Royovac heavy-duty 6 V lantern battery with screw tops was obtained from Fisher Scientific (Waltham, MA, USA) while analog panel current ammeters (0-200 μA DC) and 100 kΩ audio-taper potentiometers were bought from local stores. Male Wistar rats (200-300 g) were purchased from Charles River Laboratories (Wilmington, MA, USA) while blood glucose measuring meter (Aimstrip plus) and strips were purchased from Fisher Scientific (Pittsburgh, PA, USA). All other reagents were of analytical grade.

Caco-2 Monolayer Culture in Transwells

Caco-2 human intestinal epithelial cells (passages #5-10) were cultured in DMEM containing 10% v/v FBS and 1% v/v P/S and seeded in 24 well plate transwells at a density of 2×105 cells/ml. 200 μl DMEM with cells was placed in apical side while 600 μl cell free DMEM was placed in the basolateral side. The cells were allowed to grow for a period of 18-21 days and medium replaced with fresh DMEM every other day. TEER was measured on a regular basis and when it reached above 200 Ωcm2, indicating sufficient tight junction integrity between the cells in the monolayer, iontophoretic transport study of insulin was performed [11, 12].

Circuit Setup and FITC-Insulin Transport Assay

The circuit for in vitro transport study was set up as shown in FIG. 1. To maintain sterile conditions, all in vitro experiments including circuit set up were done under aseptic conditions in a biosafety cabinet. A 6 V battery was used to supply electrical current to transwells containing Caco-2 monolayer. The higher potential of the battery was connected to the basolateral side of the transwell while the lower potential of the battery was connected to the apical side while taking care not to touch the transwell membranes with Caco-2 cell monolayer. The current applied to the cell was monitored by an ammeter and its value was adjusted to 50 μA using a potentiometer. Three different branches, each attached to an ammeter, potentiometer and transwell were connected in parallel across the battery to enable three different measurements at a time.

Transport experiments were carried out in triplicates and at least 3 transwells were used per trial for each group. Before the start of the experiment, the existing medium in the transwell was replaced with phenol red, FBS and P/S free DMEM in both the apical (200 μl) and basolateral side (600 μl) and the cells were incubated for 30 min. At the start of study, the medium in the apical side was replaced with 200 μl of 500 μg/ml FITC-insulin prepared in phenol red, FBS and P/S free DMEM. Immediately after addition of FITC-insulin at the apical side, a 100 μl aliquot was withdrawn from the basolateral side and replaced with same volume fresh DMEM. This was performed at 0.25, 0.5, 1, 2, 3 and 5 h. A 50 μA electric current was applied to the cells during the first hour of the study for a period of 10 min, followed by a 10 min recovery period and this was repeated another two times. At the end of 1 h (total 30 min iontophoresis), the transwell plates were kept inside an incubator at 37° C., 5% CO2 and only taken out to remove 100 μl aliquots from the basolateral side followed by replacement with same volume fresh medium at the aforementioned time periods. After the end of study at 5 h, the FITC-insulin concentration in the aliquots were measured at 495/520 nm excitation/emission wavelengths using a Tecan Infinite M200 Pro multimode reader (Tecan US, Inc., Morrrisville, NC, USA microplate reader). Results were plotted as % FITC-insulin transport vs time. TEER was measured at every time point when aliquots were withdrawn from the transwells. Apparent permeability coefficient (Papp) was calculated using the equation [13]:

$$P_{app} = \frac{dQ}{dt} \times \frac{1}{A \cdot C0}.$$

where dQ/dt is calculated from the slope of cumulative insulin transport across Caco-2 cells with respect to time, A is the area of the transwell surface and C0 is the insulin concentration in the apical side at time 0. The transport enhancement ratio (ER) was calculated using the equation [13]:

$$ER = \frac{P_{app} Iontophoresis}{P_{app} \; control}$$

Confocal Microscopy

For qualitative analysis of FITC-insulin uptake by Caco-2 cells, the transwells from FITC-insulin transport study were washed two times with HBSS, followed by addition of 100 μl of 4% paraformaldehyde and kept at 4° C. overnight. On the next day, the transwells were washed with HBSS and the membrane cut out and placed in glass slides. Mounting media with DAPI was added to the membranes and covered with glass slides. Confocal imaging was performed using Olympus Fluoview 1000™ Spectral Confocal instrument at 60× magnification.

Insulin Mucoadhesive Patch Preparation

Insulin mucoadhesive patches were prepared as documented earlier [4]. Briefly, Eudragit E PO, pectin and SCMC were mixed in the ratio of 1:1:2 and known quantity of insulin was added to the mixture. About 110 mg of the mixture was pressed at 3-ton pressure using a hydraulic press into a patch. The patches were then cut into 5×3 mm (length×breadth) sized rectangular smaller patches. One side of the patch was completely covered with aluminum foil using minimal amount of super glue placed at one corner of the foil. Wires with a small section of their protective insulation removed were then stuck on the aluminum foil using super glue. Care was taken not to cover the entire wire placed over the foil with super glue. The exposed wire sticking on to the patches were then taped with an electrical insulating tape to prevent any loss of current in vivo through exposed wire. The insulin doses used in the patches were either 25 or 50 U/kg.

Circuit Setup and In Vivo Efficacy Study of Intestinal Iontophoresis Using Insulin Mucoadhesive Patches All animal experiments were performed in accordance with the University of California Santa Barbara animal care committee guidelines and to the Guide for the Care and Use of Animals of the Institute of Laboratory Animal Resources, National Research Council.

The circuit for in vivo experiments was set up as illustrated in FIG. 3. Intestinal iontophoresis was carried out using a 6 V battery connected to the intestine. A potentiometer and an ammeter were used in the electrical circuit to accurately control and measure the electric current. Given that the identified safe threshold for iontophoresis is 0.5 mA/cm2, the electrical parameters were selected in order to perform the studies using a safe current density of 0.33 mA/cm2 [8]. For the experiment, the rats were fasted overnight but given free access to water. Prior to the start of intestinal iontophoresis, the rats were anesthetized, a portion of abdomen prepped for surgery and an incision was made in the area to expose the intestine. Experiments were conducted using sterile instruments and following good surgical practices.

Two small cuts about 5 cm afar were made in a small exposed section of the intestine and patches containing 50 U/kg insulin connected to wires and battery source were inserted. Thereafter current (45-50 μA) was allowed to flow for 1.5 min followed by 3.5 min of recovery time for 1 h, amounting to a total 18 min of iontophoresis. After 1 h, the patches were left in place but the wires were disconnected from the battery and cut close to the inserted patches. The intestinal incisions with the patches left in place were stitched, the intestine put back into the abdomen and the muscle and skin sutured. Blood glucose was determined at the start of the study and at every 0.5 h till the end of study at 3 h. The rats were kept anesthetized till the end of experiment. Afterwards, the animals were euthanized and the intestinal sections in and around the patches were dissected for further histological examination to determine morphological changes, if any, due to iontophoresis.

Control experiments with no electric current were conducted similarly. Additionally, subcutaneous (SQ) administration of 1 U/kg insulin solution was performed in 3 rats for comparison of efficacy. To determine whether decrease in current or insulin dose would bring about similar efficacy, studies were conducted using 50 μA current with patches containing 25 U/kg insulin or using 25 μA current with 50 U/kg insulin patches.

Tissue Histology

Tissues were fixed in 10% buffered formalin, dehydrated in ethanol, and embedded in paraffin. Five-micron cross-sections of intestine tissues were deparaffinzed, rehydrated, and stained with hematoxylin and eosin. Histological morphology was examined using a light microscope (Olympus BX60 Upright Compound Microscope).

Statistical Analysis

All in vitro data are presented as mean±standard deviation (SD) while in vivo data are presented as mean±standard error (SE). The statistical analyses were performed using two-tailed student's t-test and p value <0.05 was considered statistically significant. Graphs were plotted using Graphpad Prism™ 6.0, (GraphPad Software, La Jolla, CA).

Results

FITC-Insulin Transport

The transport of FITC-insulin across Caco-2 monolayers upon application of electric current was first assessed. Transport was higher with electric current right from the onset of study at 15 min (1.2 μg in electric current group compared to 0.2 µg in control group) but it improved significantly (p<0.01-0.05) from 2 h onwards (FIG. 4). At the end of 5 h, approximately 14.1 µg FITC-insulin was transported across the cells to which electric current was applied compared to only about 5.5 µg transport in control group. The Papp of FITC-insulin across the cells in 5 h was 26.4×10-7 cm/s with electricity while that without electricity was 9.9×10-7 cm/s. The Papp value of insulin in control cells was very comparable to those obtained by other researchers using 21-day Caco-2 monolayer cultures [12, 14, 15]. The enhancement ratio calculated from the Papp was 2.7.

Measurement of Tight Junction Integrity in Caco-2 Monolayers Upon Application of Electric Current TEER was measured to determine the tight junction integrity in Caco-2 cells upon application of electric current. TEER decreased significantly (p<0.05) by 10% within 15 min of passage of current compared to no specific decrease in the control group (FIG. 5). After 2 h of the study, TEER dropped more significantly by 35% of initial levels (65.7±3.8%) and was relatively constant during the remaining 3 h of the study. In comparison, in control (no current) wells, TEER reduced by around 9 and 4% of initial levels in 2 and 3 h respectively (91.2±1.1% and 95.6±6.5%).

Confocal Micrograph Images

Confocal laser scanning microscopy images of transwell membranes of wells with or without iontophoresis showed higher uptake of FITCmsulin by cells exposed to electric current compared to control wells (data not shown).

In Vivo Intestinal Iontophoresis Using Mucoadhesive Patches

After in vitro evaluation of intestinal iontophoresis of insulin, studies were conducted in vivo. Rats with 50 U/kg insulin patches inserted in their intestine and subjected to 45-50 µA current, demonstrated a significant (p<0.01) drop in blood glucose levels from 2 h onwards to 35% of initial levels (65±2.2%) that further decreased to 63% (36.6±3%) in 3 h (FIG. 6). In contrast, rats with 50 U/kg insulin patches but without electric current treatment, showed only 3.4% drop in 2 h (96.4±6.6%) followed by a maximum 12% drop in 3 h (88.1±6.7%). Rats that were intra-intestinally injected with 50 U/kg insulin solution did not show any drop in blood glucose levels with time while those subcutaneously injected with 1 U/kg insulin solution showed a maximum drop of 42% in 1.5 h (57.9±4.1%) that recovered to about 17% of initial levels (83.3±2.6%) in 3 h.

Effect of Varying Electrical Current and Insulin Dose on Blood Glucose Reduction The considerable drop in blood glucose levels upon application of electric current as observed in FIG. 6, prompted us to investigate whether similar efficacy could be achieved using lower current or insulin dose. To this end, we halved the current to 20-25 µA keeping the duration of current and insulin dose same (18 min and 50 U/kg respectively) and determined drop in blood glucose in 3 h. Lowering the current value to 20-25 µA did not bring about an extensive drop in blood glucose and a maximum 26% (74.04±14.2% of initial level) decrease was noted in 3 h (FIG. 7). In comparison, same dose-no electric current control rats demonstrated only 12% (88.1±6.7% of initial level) drop in blood glucose in 3 h. Next, blood glucose lowering efficacy by reducing insulin dose to 25 U/kg but keeping current and treatment duration same (45-50 µA current and 18 min respectively) was investigated. This modification also did not bring about a substantial drop in blood glucose levels and a maximum decrease of 23% (77.1±8.8% of initial level) in 3 h was observed while its respective no electric current control resulted in a 15% drop (85±12.2% of initial level).

Assessment of Toxicity to Intestinal Tissue Upon Application of Electric Current Histological examination showed no difference with regard to morphology of intestinal tissue between the groups of rats with or without iontophoretic treatment (data not shown). In particular, sections where patches were placed or adjacent areas showed no structural damage upon the application of electric current. The lumen of the intestine (lamina propria and intestinal gland) was intact, and the thickness of smooth muscles was similar amongst all the tissues when measured with light microscopy.

Discussion

The oral route although very convenient for drug administration cannot be used for delivery of biologics due to their propensity to degrade by gastric acids, proteolytic cleavage by intestinal enzymes and low permeability across the intestinal wall, that results in almost negligible oral bioavailability of such drugs [33]. To circumvent the issues of gastrointestinal degradation and low intestinal permeability, various techniques have been utilized including chemical modification of biologics, use of permeation enhancers, protease inhibitors, cell penetrating peptides, nanoparticles and encapsulation in enterically coated devices amongst others. However, there is still an unmet medical need to develop technologies that will substantially improve oral delivery of biologics. To this end, we explored intestinal iontophoresis as a novel oral protein delivery modality.

Transport of insulin across intestinal cells was enhanced close to about 3-fold with the application of intermittent electric current during first hour of the study compared to no current control. This can be attributed to significant (p<0.01-0.05) decline in TEER from the onset of the experiment with a maximal 35% drop at 2 h. Interestingly, insulin transport across the cells was also significantly (p<0.01-0.05) higher than control from 2 h onwards when TEER drop was maximum. The reduction in TEER indicates that insulin transport across Caco-2 monolayer subjected to electric current is mostly paracellular. In the present study, at the end at 5 h, no significant difference in TEER between control and electric current group was observed, indicating that tight junction integrity may recover with time. In the present study, the higher transport of insulin across Caco-2 cells was corroborated by confocal images of transwell membranes that showed presence of higher FITC-insulin in cells subjected to iontophoresis. To verify the results in vivo, we performed iontophoresis at an intestinal site and observed good correlation with in vitro data.

Mucoadhesive patches loaded with 50 U/kg insulin were utilized for in vivo experiments because they had previously demonstrated to improve insulin transport across the intestine in non-diabetic rats [4, 41]. These mucoadhesive patches were placed inside enterically coated capsules that enabled them to bypass the harsh acidic environment of the stomach and release drug loaded patches from the capsules specifically in the intestine. Upon release, the mucoadhesive polymers in the patches allow strong adhesion of the patches to the mucus layer of intestine. Additionally, the patches provide a concentrated depot of therapeutics at a single location that swell in an aqueous environment and facilitate concentration gradient mediated transport of biologics across the intestine while protecting them from proteolytic degradation by forming a physical barrier and preventing access of enzymes to loaded drugs.

The objective of the present study was to investigate whether iontophoresis could further enhance the efficacy of intestinal mucoadhesive patches in oral insulin delivery. Keeping the current value similar for in vitro and in vivo experiments, we observed that iontophoresis greatly enhanced transport of insulin across the intestine leading to a remarkable 63% drop in blood glucose levels. Also, consistent with in vitro experiments, a very significant (p<0.01) drop in blood glucose levels was observed at 2 h of the study that steadily declined till 3 h when animals became severely hypoglycemic and the study was terminated.

In the present study, the intestinal samples obtained after in vivo experiments did not show signs of tissue damage. Iontophoresis works predominantly by establishing an electrical gradient for transport of molecules across pathways that already exist within a barrier, therefore any histological damage to tissues is not anticipated [51]. Also, given that the identified safe threshold for iontophoresis is 0.5 mA/cm2, a low and safe current density of 0.33 mA/cm2 or less were used in the study [8].

This study demonstrates that oral delivery of biologics can be enhanced through iontophoresis that modulates intestinal absorptive pathways to considerably improve permeability of such drugs across the intestine. The method can be practiced, e.g., using devices utilizing miniature electronic/ electrical systems such as a micro-electromechanical system (MEMS) based device or a microneedle device. For development of an intestinal iontophoretic device, insulin mucoadhesive patches with integrated circuits and on chip battery can be designed and placed in enterically coated capsules for site specific delivery of the device to intestine. Release of iontophoretic device from the capsule in the intestine followed by adhesion of mucoadhesive patches to the intestinal mucosa and exposure to the aqueous environment may be used to trigger onset of iontophoresis.

When drug load depletes leading to complete disintegration of patches and subsequent loss of mucosal adhesion, the device could be designed to safely pass through the GIT and get excreted. This study brings forth an unexplored approach for oral insulin delivery that can form the foundation for further development of this technology into clinical devices.

In summary, intestinal iontophoresis was conducted using insulin as a model drug and was found to remarkably improve insulin transport in vitro and its pharmacodynamics in vivo. A 35% drop in TEER was observed in Caco-2 monolayers subjected to iontophoresis that consequently led to almost three-fold enhancement in insulin transport across the cells. In rats, insulin loaded mucoadhesive patches integrated with iontophoretic circuit and surgically placed in the intestine, led to profound hypoglycemia that was dependent on insulin dose and current density. In addition, iontophoresis did not cause any structural damage to intestinal tissues, indicating that the technology is safe to use.

REFERENCES

[1] J. Shaji, V. Patole, Protein and peptide drug delivery: oral approaches, Indian J Pharm Sci 70 (3) (2008) 269-277, https://doi.org/10.4103/0250-474X.42967.

[2] P. Fonte, F. Araujo, S. Reis, B. Sarmento, Oral insulin delivery: how far are we? J. Diabetes Sci. Technol. 7 (2) (2013) 520-531.

[3] A. Banerjee, K. Ibsen, T. Brown, R. Chen, C. Agatemor, S. Mitragotri, Ionic liquids for oral insulin delivery, Proc Natl Acad Sci USA 115 (28) (2018) 7296-7301, https://doi.org/10.1073/pnas.1722338115.

[4] A. Banerjee, J. Lee, S. Mitragotri, Intestinal mucoadhesive devices for oral delivery of insulin, Bioeng. Transl. Med. 1 (2016) 338-346.

[5] V. Gupta, B. H. Hwang, J. Lee, A. C. Anselmo, N. Doshi, S. Mitragotri, Mucoadhesive intestinal devices for oral delivery of salmon calcitonin, J. Controll. Release 172 (3) (2013) 753-762, https://doi.org/10.1016/j.jconrel.2013.09.004.

[6] J. B. Sloan, K. Soltani, Iontophoresis in dermatology: a review, J. Am. Acad. Dermatol. 15 (4, Part 1) (1986) 671-684 October 1986.

[7] M. R. Prausnitz, R. Langer, Transdermal drug delivery, Nat. Biotechnol. 26 (11) (2008) 1261-1268, https://doi.org/10.1038/nbt.1504.

[8] N. Dixit, V. Bali, S. Baboota, A. Ahuja, J. Ali, Iontophoresis—an approach for controlled drug delivery: a review, Curr. Drug Deliv. 4 (1) (2007) 1-10.

[9] S. Singh, J. Singh, Transdermal drug delivery by passive diffusion and iontophoresis: a review, Med. Res. Rev. 13 (5) (1993) 569-621.

[10] O. Pillai, N. Kumar, C. S. Dey, Sivaprasad N. Borkute, R. Panchagnula, Transdermal iontophoresis of insulin: III. Influence of electronic parameters, Methods Find Exp Clin Pharmacol 26 (6) (2004) 399-408 831314 [pii].

[11] B. Srinivasan, A. R. Kolli, M. B. Esch, H. E. Abaci, M. L. Shuler, J. J. Hickman, TEER measurement techniques for in vitro barrier model systems, J Lab Autom 20 (2) (2015) 107-126, https://doi.org/10.1177/2211068214561025.

[12] C. Tang, J. Yu, L. Yin, C. Yin, Y. Pei, Transport of insulin in modified Valia-Chien chambers and Caco-2 cell monolayers, Drug Dev. Ind. Pharm. 33 (4) (2007) 449-456 (DOI:779019922 [pii).

[13] V. Gupta, B. H. Hwang, N. Doshi, S. Mitragotri, A permeation enhancer for increasing transport of therapeutic macromolecules across the intestine, J. Controll. Release 172 (2) (2013) 541-549, https://doi.org/10.1016/j.jconrel.2013.05.002.

[14] R. L. DiMarco, D. R. Hunt, R. E. Dewi, S. C. Heilshorn, Improvement of paracellular transport in the Caco-2 drug screening model using protein-engineered substrates, Biomaterials 129 (2017) 152-162 DOI:S0142-9612(17) 30164-3 [pii].

[15] R. Greenwood, A. Al-achi, Human insulin diffusion profile through a layer of Caco-2 cells, Drug Dev. Ind. Pharm. 23 (2) (1997) 221-224, https://doi.org/10.3109/03639049709149796.

[16] H. Kalluri, A. K. Banga, Transdermal delivery of proteins, AAPS PharmSciTech 12 (1) (2011) 431-441, https://doi.org/10.1208/s12249-011-9601-6.

[17] Y. N. Kalia, A. Naik, J. Garrison, R. H. Guy, Iontophoretic drug delivery, Adv Drug Deliv Rev 56 (5) (2004) 619-658, https://doi.org/10.1016/j.addr.2003.10.026.

[18] G. G. Philip, Iontophoretic delivery of peptide drugs, J. Control. Release 41 (1-2) (1996) 33-48, https://doi.org/10.1016/0168-3659(96)01354-5.

[19] M. B. Brown, G. P. Martin, S. A. Jones, F. K. Akomeah, Dermal and transdermal drug delivery systems: current and future prospects, Drug Deliv. 13 (3) (2006) 175-187 (DOI:N45362P167475H46 [pii]).

[20] A. Z. Alkilani, M. T. McCrudden, R. F. Donnelly, Transdermal drug delivery: innovative pharmaceutical developments bdsed on disruption of the barrier properties of the stratum corneum, Pharmaceutics 7 (4) (2015) 438-470, https://doi.org/10.3390/pharmaceutics7040438.

[21] W. Martanto, S. P. Davis, N. R. Holiday, J. Wang, H. S. Gill, M. R. Prausnitz, Transdermal delivery of insulin using microneedles in vivo, Pharm. Res. 21 (6) (2004) 947-952.

[22] S. Mitragotri, Current status and future prospects of needle-free liquid jet injectors, Nat Rev Drug Discov 5 (7) (2006) 543-548, https://doi.org/10.1038/nrd2076.

[23] Y. Chen, Y. N. Kalia, Short-duration ocular iontophoresis of ionizable aciclovir prodrugs: a new approach to treat herpes simplex infections in the anterior and posterior segments of the eye, Int. J. Pharm. 536 (1) (2018) 292-300 30 Jan. 2018.

[24] Korsten M A, Lyons B L, Radulovic M, Cummings T M, Sikka G, Singh K, et al., Delivery of neostigmine and glycopyrrolate by iontophoresis: a nonrandomized study in individuals with spinal cord injury, Spinal Cord. (2017) https://doi.org/10. 1038/s41393-017-0018-2.

[25] F. Gaillard-Bigot, M. Roustit, J. F. Jourdil, F. Stanke-Labesque, J. L. Cracowski, Vascular effects of treprostinil cutaneous iontophoresis on the leg, finger, and foot, J. Clin. Pharmacol. 57 (9) (2017) 1215-1220, https://doi.org/10.1002/jcph.898.

[26] M. E. Myles, D. M. Neumann, J. M. Hill, Recent progress in ocular drug delivery for posterior segment disease: emphasis on transscleral iontophoresis, Adv. Drug Deliv. Rev. 57 (14) (2005) 2063-2079 (DOI:S0169-409X(05)00171-7 [pii]).

[27] N. Shoeibi, M. Mandizadeh, M. Shafiee, Iontophesis in opthalmology: a review of the literature, Rev. Clin. Med. 1 (4) (2014) 183-188, https://doi.org/10.17463/RCM.2014.04.003.

[28] H. Zhang, J. Zhang, J. B. Streisand, Oral mucosal drug delivery: clinical pharmacokinetics and therapeutic applications, Clin. Pharmacokinet. 41 (9) (2002) 661-680 (DOI:410903 [pii].

[29] W. Ren, A. Baig, D. J. White, S. K. Li, Characterization of cornified oral mucosa for iontophoretically enhanced delivery of chlorhexidine, Eur. J. Pharm. Biopharm. 99 (2016) 35-44, https://doi.org/10.1016/j.ejpb.2015.11.005.

[30] A. Jacoby, DerBrucke M G, Vaginal iontophoresis of a choline compound, Am. J. Obstetr. Gynecol. 44 (2) (1942) 250-258. August 1942.

[31] M. Leonard, E. Creed, D. Brayden, A. W. Baird, Evaluation of the Caco-2 monolayer as a model epithelium for iontophoretic transport, Pharm. Res. 17 (10) (2000) 1181-1188.

[32] M. Leonard, E. Creed, D. Brayden, A. W. Baird, Iontophoresis-enhanced absorptive flux of polar molecules across intestinal tissue in vitro, Pharm. Res. 17 (4) (2000) 476-478.

[33] M. Goldberg, I. Gomez-Orellana, Challenges for the oral delivery of macromolecules, Nat. Rev. Drug Discov. 2 (4) (2003) 289-295, https://doi.org/10.1038/nrd1067.

[34] A. Manosroi, T. Tangjai, C. Sutthiwanjampa, W. Manosroi, R. G. Werner, F. Gotz, et al., Hypoglycemic activity and stability enhancement of human insulin-tat mixture loaded in elastic anionic niosomes, Drug Deliv. 23 (8) (2016) 3157-3167, https://doi.org/10.3109/10717544.2016.1157840.

[35] B. Sarmento, A. Ribeiro, F. Veiga, D. Ferreira, R. Neufeld, Oral bioavailability of insulin contained in polysaccharide nanoparticles, Biomacromolecules 8 (10) (2007) 3054-3060, https://doi.org/10.1021/bm0703923.

[36] B. Sarmento, A. Ribeiro, F. Veiga, P. Sampaio, R. Neufeld, D. Ferreira, Alginate/chitosan nanoparticles are effective for oral insulin delivery, Pharm Res. 24 (12) (2007) 2198-2206, https://doi.org/10.1007/s11095-007-9367-4.

[37] M. A. Radwant, H. Y. Aboul-Enein, The effect of oral absorption enhancers on the in vivo performance of insulin-loaded poly(ethylcyanoacrylate) nanospheres in diabetic rats, J Microencapsul. 19 (2) (2002) 225-235, https://doi.org/10.1080/02652040110081406.

[38] A. Banerjee, J. Wong, R. Gogoi, T. Brown, S. Mitragotri, Intestinal micropatches for oral insulin delivery, J Drug Target (2017) 1-8, https://doi.org/10.1080/1061186X.2017.1300664.

[39] R. Schaffnit, P. Wicklandt, F. Moll, Controlled iontophoretic release of glucocorticoids through epithelial cell monolayers, J. Control. Release 54 (1) (1998) 9-14 1 Jun. 1998.

[40] H. Sekijima, J. Ehara, Y. Hanabata, T. Suzuki, S. Kimura, V. H. Lee, et al., Characterization of ocular iontophoretic drug transport of ionic and non-ionic compounds in isolated Rabbit Cornea and Conjunctiva, Biol Pharm Bull. 39 (6) (2016) 959-968, https://doi.org/10.1248/bpb.b15-00932.

[41] A. Banerjee, S. Mitragotri, Intestinal patch systems for oral drug delivery, Curr. Opin. Pharmacol. 36 (Supplement C) (2017) 58-65 October 2017.

[42] S. Tokumoto, N. Higo, K. Sugibayashi, Effect of electroporation and pH on the iontophoretic transdermal delivery of human insulin, Int. J. Pharm. 326 (1-2) (2006) 13-19 (DOI:S0378-5173(06)00551-5 [pii].

[43] O. Pillai, V. Nair, R. Panchagnula, Transdermal iontophoresis of insulin: IV. Influence of chemical enhancers, Int. J. Pharm. 269 (1) (2004) 109-120 DOI: S037851730300526X [pii].

[44] Y. Pan, H. Y. Zhao, J. M. Zheng, The enhancing effect of electroporation and iontophoresis on the permeation of insulin through human skin, Yao Xue Xue Bao. 37 (8) (2002) 649-652.

[45] H. Chen, H. Zhu, J. Zheng, D. Mou, J. Wan, J. Zhang, et al., Iontophoresis-driven penetration of nanovesicles through microneedle-induced skin microchannels for enhancing transdermal delivery of insulin, J. Control. Release 139 (1) (2009) 63-72, https://doi.org/10.1016/j.jconrel.2009.05.031.

[46] A. Chaturvedula, D. P. Joshi, C. Anderson, R. L. Morris, W. L. Sembrowich, A. K. Banga, In vivo iontophoretic delivery and pharmacokinetics of salmon calcitonin, Int. J. Pharm. 297 (1) (2005) 190-196 13 Jun. 2005.

[47] S. Dubey, Y. N. Kalia, Electrically-assisted delivery of an anionic protein across intact skin: cathodal iontophoresis of biologically active ribonuclease T1, J. Control. Release 152 (3) (2011) 356-362 30 Jun. 2011.

[48] Y. Huang, S. Wu, Transdermal iontophoretic delivery of thyrotropin-releasing hormone across excised rabbit pinna skin, Drug Dev. Ind. Pharm. 22 (11) (1996) 1075-1081, https://doi.org/10.3109/03639049609065943.

[49] F. F. Behar-Cohen, A. El Aouni, S. Gautier, G. David, J. Davis, P. Chapon, et al., Transscleral Coulomb-controlled iontophoresis of methylprednisolone into the rabbit eye: influence of duration of treatment, current intensity and drug concentration on ocular tissue and fluid levels, Exp. Eye Res. 74 (1) (2002) 51-59, https://doi.org/10.1006/exer.2001.1098.

[50] M. T. Kralinger, M. Voigt, G. Kieselbach, D. Hamasaki, B. Hayden, J. M. Parel, Ocular delivery of acetylsalicylic acid by repetitive coulomb-controlled iontophoresis, Ophthalmic Res. 35 (2) (2003) 102-110, https://doi.org/10.1159/000069129.

[51] E. B. Ghartey-Tagoe, J. S. Morgan, A. S. Neish, M. R. Prausnitz, Increased permeability of intestinal epithelial monolayers mediated by electroporation, J. Control. Release 103 (1) (2005) 177-190 2 Mar. 2005.

[52] H. J. Lee, N. Choi, E. Yoon, I. Cho, MEMS devices for drug delivery, Adv. Drug Deliv. Rev. 128 (2018) 132-147. Available online 5 Nov. 2017, Published: Mar. 15, 2018.

[53] Y. Zhuang, W. Hou, X. Zheng, Z. Wang, J. Zheng, X. Pi, et al., A MEMS-based electronic capsule for time controlled drug delivery in the alimentary canal, Sensors Actuators A Phys. 169 (1) (2011) 211-216 10 Sep. 2011.

[54] P. Xitian, L. Hongying, W. Kang, L. Yulin, Z. Xiaolin, W. Zhiyu, A novel remote controlled capsule for site-specific drug delivery in human GI tract, Int. J. Pharm. 382 (1) (2009) 160-164 1 Dec. 2009.

[55] Y. Zhang, Y. Chen, X. Yu, Y. Qi, Y. Chen, Y. Liu, et al., A flexible device for ocular iontophoretic drug delivery, Biomicrofluidics 10 (1) (2016) 011911, https://doi.org/10.1063/1.4942516.

[56] G. Traverso, C. M. Schoellhammer, A. Schroeder, R. Maa, G. Y. Lauwers, B. E. Polat, et al., Microneedles for drug delivery via the gastrointestinal tract, J Pharm Sci. 104 (2) (2015) 362-367, https://doi.org/10.1002/jps.24182.

[57] P. G. Green, R. S. Hinz, A. Kim, F. C. Szoka Jr., R. H. Guy, Iontophoretic delivery of a series of tripeptides across the skin in vitro, Pharm. Res. 8 (9) (1991) 1121-1127.

[58] M. R. Prausnitz, V. G. Bose, R. Langer, J. C. Weaver, Electroporation of mammalian skin: a mechanism to enhance transdermal drug delivery, Proc. Natl. Acad. Sci. U.S.A. 90 (22) (1993) 10504-10508.

[59] S. Mitragotri, D. Blankschtein, R. Langer, Ultrasound-mediated transdermal protein delivery, Science 269 (5225) (1995) 850-853.

[60] S. Lee, N. Kollias, D. J. McAuliffe, T. J. Flotte, A. G. Doukas, Topical drug delivery in humans with a single photomechanical wave, Pharm. Res. 16 (11) (1999) 1717-1721.

[61] S. Henry, D. V. McAllister, M. G. Allen, M. R. Prausnitz, Microfabricated microneedles: a novel approach to transdermal drug delivery, J. Pharm. Sci. 87 (8) (1998) 922-925, https://doi.org/10.1021/js980042.

[62] C. M. Schoellhammer, A. Schroeder, R. Maa, G. Y. Lauwers, A. Swiston, M. Zervas, et al., Ultrasound-mediated gastrointestinal drug delivery, Sci. Transl. Med. 7 (310) (2015) 310ra168, https://doi.org/10.1126/scitranslmed.aaa5937.

---

We claim:

1. A method for oral drug delivery of an active agent to a subject in need thereof comprising:
   a) orally administering an iontophoretic drug delivery device to the subject, wherein the iontophoretic drug delivery device comprises:
      at least one electrode in direct contact with an outer surface of the iontophoretic drug delivery device or connected to the iontophoretic drug delivery device by an electrically conductive material,
      a drug reservoir comprising the active agent, and
      a mucoadhesive patch attached to or comprising the drug reservoir; and
   b) providing iontophoresis at an electrical current in a range from 20 to 60 µA from the at least one electrode after orally administering the iontophoretic drug delivery device.

2. The method of claim 1, wherein the drug delivery device provides iontophoresis after being triggered by an environmental stimulus, a timer, or a remote control.

3. The method of claim 2, wherein at least two electrodes attach to a wall of the intestine, following step (a).

4. The method of claim 2, wherein the active agent is released concurrently with the iontophoresis.

5. The method of claim 2, wherein the iontophoresis is provided or performed in one or more cycles of iontophoresis.

6. The method of claim 5, wherein a cycle comprises delivering electrical current for a period of time ranging from 0.5 to 20 minutes followed by a recovery time period ranging from 0.5 to 20 minutes.

7. The method of claim 2, wherein iontophoresis is provided for longer than 30 minutes and less than 24 hours.

8. The method of claim 1, wherein following step (a), the drug delivery device adheres to the intestinal mucosa.

9. The method of claim 1, wherein a biocompatible protective coating is released from the drug delivery device to uncover the electrodes prior to providing iontophoresis.

10. The method of claim 9, wherein the biocompatible protective coating is an enteric coating that dissolves or degrades before or upon reaching the intestine.

11. The method of claim 1, wherein the active agent is a small molecule or macromolecule.

12. The method of claim 1, wherein the subject has type 1 or type 2 diabetes and the active agent is insulin or an analog thereof.

13. The method of claim 12, wherein the active agent is administered in an effective amount to reduce blood glucose levels.

14. The method of claim 1, wherein the active agent is administered or present in the device at a dosage of from 1 U/kg to 100 U/kg.

15. A system for oral drug delivery of an active agent to a subject in need thereof comprising:
   a) an intestinal iontophoretic device comprising:
      a capsule;
      at least two electrodes in direct contact with the outer surface of the capsule or connected to the capsule by an electrically conductive material; and inside the capsule:
a mucoadhesive patch, and
an active agent;
b) a control unit in electrical communication with the electrodes of the intestinal iontophoretic device configured to provide an electrical current in a range from 20 to 60 µA.

16. The system of claim 15, wherein the capsule comprises an outer enteric biocompatible protective coating.

17. The system of claim 15, further comprising an active agent release trigger in or on the capsule.

* * * * *

SEQUENCE LISTING

```
<160> NUMBER OF SEQ ID NOS: 4

<210> SEQ ID NO 1
<211> LENGTH: 180
<212> TYPE: PRT
<213> ORGANISM: Homo sapiens

<400> SEQUENCE: 1

Met Lys Ser Ile Tyr Phe Val Ala Gly Leu Phe Val Met Leu Val Gln
1               5                   10                  15

Gly Ser Trp Gln Arg Ser Leu Gln Asp Thr Glu Glu Lys Ser Arg Ser
            20                  25                  30

Phe Ser Ala Ser Gln Ala Asp Pro Leu Ser Asp Pro Asp Gln Met Asn
        35                  40                  45

Glu Asp Lys Arg His Ser Gln Gly Thr Phe Thr Ser Asp Tyr Ser Lys
    50                  55                  60

Tyr Leu Asp Ser Arg Arg Ala Gln Asp Phe Val Gln Trp Leu Met Asn
65                  70                  75                  80

Thr Lys Arg Asn Arg Asn Asn Ile Ala Lys Arg His Asp Glu Phe Glu
                85                  90                  95

Arg His Ala Glu Gly Thr Phe Thr Ser Asp Val Ser Ser Tyr Leu Glu
            100                 105                 110

Gly Gln Ala Ala Lys Glu Phe Ile Ala Trp Leu Val Lys Gly Arg Gly
        115                 120                 125

Arg Arg Asp Phe Pro Glu Glu Val Ala Ile Val Glu Glu Leu Gly Arg
    130                 135                 140

Arg His Ala Asp Gly Ser Phe Ser Asp Glu Met Asn Thr Ile Leu Asp
145                 150                 155                 160

Asn Leu Ala Ala Arg Asp Phe Ile Asn Trp Leu Ile Gln Thr Lys Ile
                165                 170                 175

Thr Asp Arg Lys
            180

<210> SEQ ID NO 2
```

```
<211> LENGTH: 37
<212> TYPE: PRT
<213> ORGANISM: Homo sapiens

<400> SEQUENCE: 2

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg Gly
        35

<210> SEQ ID NO 3
<211> LENGTH: 30
<212> TYPE: PRT
<213> ORGANISM: Homo sapiens

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 4
<211> LENGTH: 31
<212> TYPE: PRT
<213> ORGANISM: Homo sapiens

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30
```